US011344686B2

(12) United States Patent
Pell et al.

(10) Patent No.: US 11,344,686 B2
(45) Date of Patent: May 31, 2022

(54) METHOD OF RESPIRATORY SYSTEM TREATMENT

(71) Applicant: BN INTELLECTUAL PROPERTIES, INC., St. Petersburg, FL (US)

(72) Inventors: Donald M. Pell, St. Petersburg, FL (US); Frank Caiazzo, Brooksville, FL (US); Paula Pell, St. Petersburg, FL (US); Govindan P. Nair, Seminole, FL (US); Michael P. Spuza, Largo, FL (US)

(73) Assignee: BN INTELLECTUAL PROPERTIES, INC., St. Petersburg, FL (US)

( * ) Notice: Subject to any disclaimer, the term of this patent is extended or adjusted under 35 U.S.C. 154(b) by 0 days.

(21) Appl. No.: 16/937,063

(22) Filed: Jul. 23, 2020

(65) Prior Publication Data
US 2020/0353187 A1 Nov. 12, 2020

Related U.S. Application Data

(63) Continuation-in-part of application No. 16/230,992, filed on Dec. 21, 2018, now Pat. No. 10,729,648.

(51) Int. Cl.
*A61M 15/00* (2006.01)
*A61M 11/00* (2006.01)
*A61L 2/00* (2006.01)
*A61L 2/24* (2006.01)

(52) U.S. Cl.
CPC ....... *A61M 15/0085* (2013.01); *A61L 2/0094* (2013.01); *A61L 2/24* (2013.01); *A61M 11/005* (2013.01); *A61L 2202/14* (2013.01); *A61L 2202/15* (2013.01); *A61M 15/0021* (2014.02); *A61M 2205/0294* (2013.01); *A61M 2205/18* (2013.01); *A61M 2205/3592* (2013.01); *A61M 2205/50* (2013.01); *A61M 2205/581* (2013.01); *A61M 2205/582* (2013.01); *A61M 2205/587* (2013.01); *A61M 2205/8206* (2013.01)

(58) Field of Classification Search
CPC .... A61L 2/24; A61M 15/0085; A61M 11/005
IPC .................. A61L 2/24; A61M 15/0085,11/005
See application file for complete search history.

(56) References Cited

U.S. PATENT DOCUMENTS

| 7,360,536 B2* | 4/2008 | Patel ................. A61M 15/0065 128/200.14 |
| 2004/0256745 A1 | 12/2004 | Simler |
| 2005/0220720 A1* | 10/2005 | Edwards ................ A61K 9/008 424/46 |
| 2017/0348494 A1 | 12/2017 | Havercroft |

OTHER PUBLICATIONS

Google scholar search_9-7-2020_inhalation of ethanol for covid (Year: 2020).*
T. Shintake. Possibility of Disinfection of SARS-CoV-2 (COVID-19) in Human Respiratory Tract by Controlled Ethanol Vapor. Inhalation. arXiv preprint arXiv:2003.12444 (2020); available on the internet Mar. 13, 2020 (Year: 2020).*
"Vapshot", downloaded Sep. 7, 2020 from the Vapshot web site at https://vapshot.com/pages/learn-more and https://vapshot.com/pages/faq, copyright 2018 (Year: 2018).*
A. Ari. "Jet, Ultrasonic, and Mesh Nebulizers: An Evaluation of Nebulizers for Better Clinical Outcomes," Eurasian Journal of Pulmonology 2014; 16: 1-7. (Year: 2014).*
"Breathing Patterns", from Medicine Libre Texts [online], downloaded Sep. 8, 2020 from https://med.libretexts.org/Bookshelves/Anatomy_and_Physiology/Book%3A_Anatomy_and_Physiology_(Boundless)/21%3A_Respiratory_System/21.5%3A_Mechanics_of_Breathing/21.5D%3A_Breathing_Patterns; (Year: 2020).*
J. T. Kelly, B. Asgharian, J. S. Kimbell, and B. A. Wong. "Particle Deposition in Human Nasal Airway Replicas Manufactured by Different Methods. Part I: Inertial Regime Particles,"Aerosol Science and Technology, 2004 38, 1063-1071. (Year: 2004).*
Ari, A., Jet, Ultrasonic, and Mesh Nebulizers: An Evaluation of Nebulizers for Better Clinical Outcomes, Eurasian Journal of Pulmonology 2014; 16: 1-7. (Year: 2014).
The Good and the Bad of Vaporizing and Inhaling Alcohol, TheMedicineJournal.com, Apr. 9, 2014, pp. 1-14, https://www.todayifoundout.com/index.php/2014/04/good-bad-vaporizing-inhaling-alcohol/.
Sisson, Joseph H., "Alcohol and Airways Function in Health and Disease," HHS Public Access, Alcohol, Aug. 30, 2007, 41(5): pp. 293-307, https://www.ncbi.nim.nih.gov/pmc/articles/PMC2081157/.
Maclean et al., Robert R., "Inhalation of Alcohol Vapor: Measurement and Implications," HHS Public Access, Alcohol Clin Exp Res, Jan. 5, 2017, 41(2): pp. 238-250, https://www.ncbi.nlm.nih.gov/pmc/articles/PMC6143144/.

* cited by examiner

*Primary Examiner* — Michael P Cohen
(74) *Attorney, Agent, or Firm* — Hauptman Ham, LLP

(57) ABSTRACT

A method of treating respiratory system tissue, includes operations of generating a plume of particles of a treating solution from a nebulizer, inhaling particles of the treating solution, delaying exhalation of an inhalation having particles of the treating solution therein, and determining whether a dose of the treating solution has been delivered, wherein the treating solution is a solution of at least 40% ethyl alcohol, by volume.

18 Claims, 13 Drawing Sheets

200

```
        ┌─────────────────────────┐
        │ 205 Determine           │  Yes   ┌──────────────────┐
    ┌──▶│ whether an operation    │──────▶│ 240 End nebulizer │
    │   │ limit is exceeded       │        │ operation         │
    │   └─────────────────────────┘        └──────────────────┘
    │              │ No
    │              ▼
    │   ┌─────────────────────────────────────┐
    │   │ 210 Position an active mesh of a    │
    │   │ nebulizer in contact with an ethyl  │
    │   │ alcohol solution.                   │
    │   └─────────────────────────────────────┘
    │              │
    │              ▼
    │   ┌─────────────────────────────────────┐
    │   │ 215 Active the active mesh to       │
    │   │ perform a cleaning operation.       │
    │   └─────────────────────────────────────┘
    │              │
    │              ▼
    │   ┌─────────────────────────┐
    │   │ 220 Determine whether   │         ┌──────────┐
    │   │ inhalation is occurring │────────▶│ 222 Wait │
    │   └─────────────────────────┘         └──────────┘
    │              │ Yes                         │
    │              ▼                             │
    │   ┌─────────────────────────────────────┐ │
    │   │ 225 Activate the active mesh to     │ │
    │   │ perform a volatilization operation. │ │
    │   └─────────────────────────────────────┘ │
    │              │                             │
    │              ▼                             │
    │   ┌─────────────────────────────────────┐ │
    │   │ 230 During the volatilization       │◀┘
    │   │ operation, direct a stream of       │
    │   │ solution particles into a flow of   │
    │   │ air for respiration.                │
    │   └─────────────────────────────────────┘
    │              │
    │              ▼
    │   ┌─────────────────────────────────────┐
    │   │ 235 Terminate the volatilization    │
    │   │ process                             │
    └───┴─────────────────────────────────────┘
```

| Time(s) | >0.3 | >0.5 | >0.7 | >1.0 | >2.0 | >5.0 |
|---|---|---|---|---|---|---|
| 1 | 10.02 | 19.89 | 19.17 | 30.25 | 20.68 | 0.00 |
| 2 | -0.62 | 17.79 | 19.20 | 32.92 | 30.72 | 0.00 |
| 3 | 9.70 | 19.55 | 17.07 | 28.59 | 25.08 | 0.00 |
| 4 | 24.85 | 20.38 | 16.27 | 24.48 | 14.00 | 0.00 |
| 5 | 25.02 | 20.50 | 16.87 | 26.01 | 11.60 | 0.00 |
| 6 | 24.14 | 20.05 | 16.61 | 26.72 | 12.48 | 0.00 |
| 7 | 23.77 | 18.79 | 16.77 | 27.07 | 13.60 | 0.00 |
| 8 | 17.66 | 18.37 | 17.86 | 29.75 | 16.34 | 0.02 |
| 9 | 12.41 | 18.74 | 18.85 | 31.11 | 18.84 | 0.06 |
| 10 | 6.66 | 19.34 | 19.74 | 32.90 | 21.26 | 0.10 |

1102 Vial inserted into nebulizer.

1104 Nebulizer retrieves user information from vial assembly.

1106 User information verified by nebulizer.

1108 Nebulizer dispenses medicine.

1110 User inhales medicine.

FIG. 11

METHOD OF RESPIRATORY SYSTEM TREATMENT

CROSS REFERENCE AND PRIORITY CLAIM

This application is a continuation-in-part of, and claims priority to, U.S. patent application Ser. No. 16/230,992, titled "A METHOD OF DELIVERING ALCOHOL" and filed on Dec. 21, 2018.

BACKGROUND

Infectious disease spreads by direct transmission or by direct transmission of a disease causing agent between persons. Direct transmission of an infectious agent includes person-to-person transmission of the infectious agent. Indirect transmission of the infectious agent includes contamination of an intermediary material by a first person and pickup of the infectious agent by a second person from the intermediary material. A likelihood of infection of a second person from an intermediary material is reduced when the amount of infectious agent on the intermediary material is reduced.

BRIEF DESCRIPTION OF THE DRAWINGS

FIG. 2 is a flow diagram of a method of delivering alcohol to a person that avoids hangover symptoms, according to some embodiments.

Figure 1:
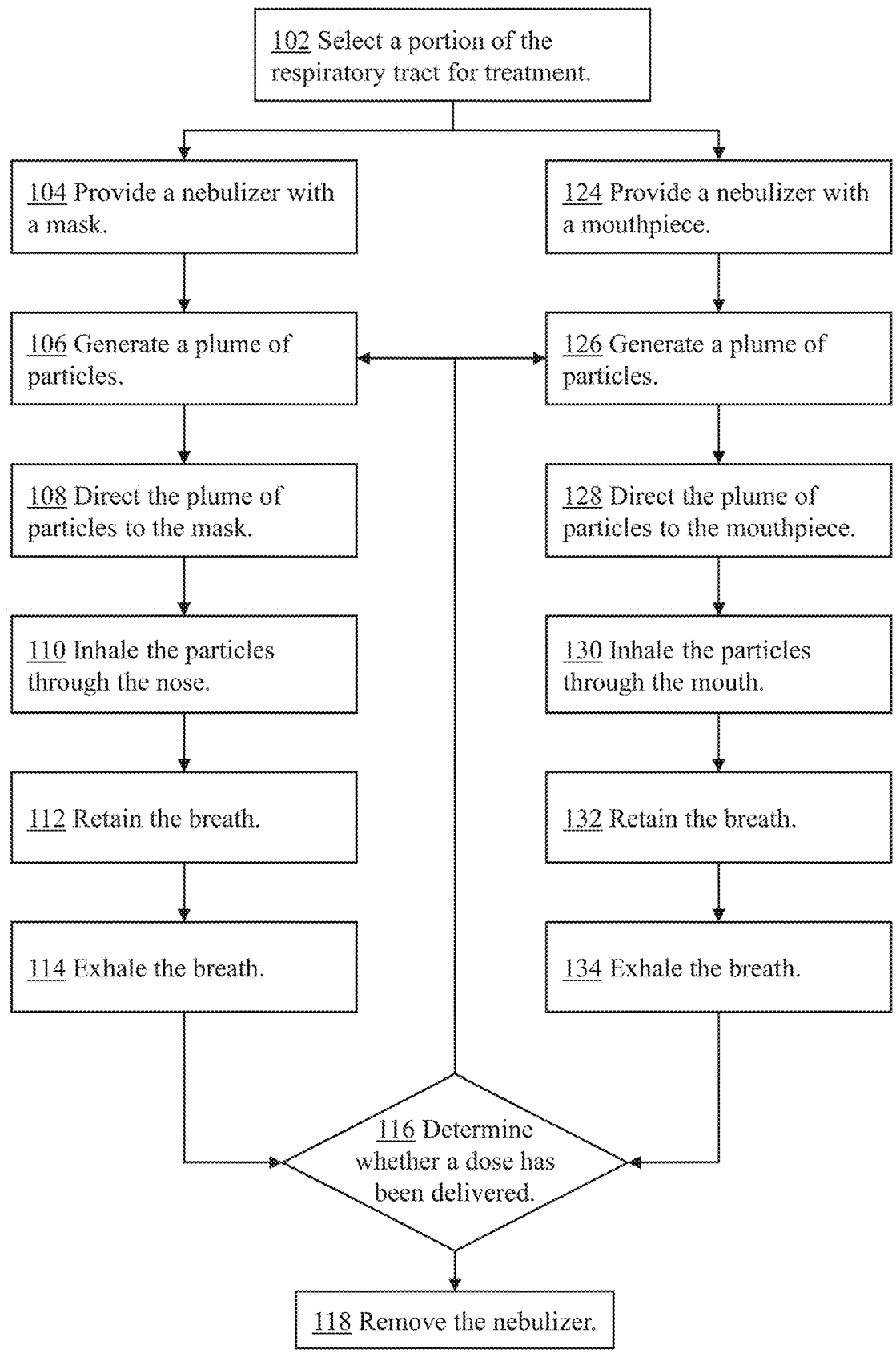
FIG. 1 is a flow diagram of a method for disinfecting interior tissue surfaces of the upper or lower respiratory system, in accordance with some embodiments.

FIG. 4 is a flow diagram of a method of operating an active mesh nebulizer, in accordance with some embodiments.

FIG. 5 is a diagram of a dosing schedule, in accordance with some embodiments.

FIG. 6 is a chart of particle sizes in a plume of particles, in accordance with some embodiments.

FIG. 7 is a table of particle size data for a plume of particles, in accordance with some embodiments.

FIGS. 8A and 8B are diagrams of a vial assembly for an active mesh nebulizer, in accordance with an embodiment.

FIGS. 9A and 9B are diagrams of an active mesh nebulizer, in accordance with an embodiment.

FIG. 10 is a flow diagram of a method of operating an active mesh nebulizer, in accordance with some embodiments.

FIG. 11 is a flow diagram of a method of operating an active mesh nebulizer, in accordance with some embodiments.

DETAILED DESCRIPTION

The following disclosure provides many different embodiments, or examples, for implementing different features of the provided subject matter. Specific examples of components, values, operations, materials, arrangements, or the like, are described below to simplify the present disclosure. These are, of course, merely examples and are not intended to be limiting. Other components, values, operations, materials, arrangements, or the like, are contemplated. The methods presented below are able to be performed with the operations described below in the order described below. In some embodiments, the order of the operations is altered without reducing the effectiveness of the method. In some embodiments, some operations of the method are omitted without reducing the effectiveness of the method. In some embodiments, additional operations are performed without reducing the effectiveness of the method.

Further, spatially relative terms, such as "beneath," "below," "lower," "above," "upper" and the like, may be used herein for ease of description to describe one element or feature's relationship to another element(s) or feature(s) as illustrated in the figure. The spatially relative terms are intended to encompass different orientations of the device in use or operation in addition to the orientation depicted in the figure. The apparatus may be otherwise oriented (rotated 90 degrees or at other orientations) and the spatially relative descriptors used herein may likewise be interpreted accordingly.

Compounds which have germicidal properties are able to destroy bacteria, viruses, or fungi. Many compounds with germicidal properties are used for cleaning surfaces in order to reduce the likelihood of transmitting an illness caused by bacteria, viruses, or fungi, to a person who comes into contact with the contaminated surface. Strong germicidal compounds, such as sodium hypochlorite, found in bleach, are able to disinfect hard surfaces with relative ease by breaking down bacteria, viruses, and fungi. Strong germicidal compounds such as sodium hypochlorite, however, are not well suited to disinfecting skin and living tissue.

Germicidal compounds such as ethyl alcohol and isopropyl alcohol are milder than sodium hypochlorite and are effective at disinfecting hard surfaces and skin. Topical treatment with ethyl or isopropyl alcohol is effective at disinfecting skin for persons exposed to bacteria, viruses, or fungi which cause illness or infectious disease. While ethyl alcohol and isopropyl alcohol are suitable for disinfecting skin, isopropyl alcohol is unsafe for ingestion. Ethyl alcohol is safe for consumption. Ethyl alcohol is effective at killing bacteria, viruses, and fungi. Internal delivery of ethyl alcohol is effective at disinfecting respiratory system tissues by killing bacteria, viruses, and fungi which have been brought into the body by breathing, and which are located on interior body surfaces of the mouth and/or respiratory system. For example, oral application of ethyl alcohol to treat conditions of the mouth is effective at reducing the bacterial count on mouth surfaces. Oral application of ethyl alcohol is performed by transferring ethyl alcohol solution in liquid form directly to the mouth and retaining the solution in the mouth (e.g., with the lips closed). The solution is then swallowed or eliminated by spitting.

Treatment of respiratory system tissue, including nasal passages, sinuses, the throat, and the lungs, involves the use of a nebulizer to produce a plume of particles (droplets) from an ethyl alcohol solution (treating solution). Particles produced by nebulizing enter the respiratory system and land on surfaces of respiratory system tissues to perform the germicidal function of the solution.

Ethyl alcohol solutions with greater than 40% ethyl alcohol are effective germicidal solutions. Solutions with greater concentrations of ethyl alcohol (e.g., between 60% and 90%) ethyl alcohol have greater effectiveness than solutions having between 40% and 60% ethyl alcohol. The germicidal characteristics of ethyl alcohol solutions are maintained whether the solution is in bulk liquid form or in droplet form.

The diameter of ethyl alcohol solution particles is related to the respiratory system tissues on which the particles land, and which are disinfected by the particles. In some embodiments, large particles, as described below, are produced by a jet-type nebulizer, where ethyl alcohol solution is placed in a reservoir and compressed gas agitates and/or passes through the solution to produce a plume of particles (e.g., a mist) which is inhaled for treatment. In some embodiments, smaller particles, as described below, are produced by active mesh nebulizers. Active mesh nebulizers produce particles by vibrating a piezoelectric plate (a mesh, or grid) with application of an electrical current to force particles or droplets of a bulk liquid against one side of the vibrating piezoelectric plate through small openings in the plate. The diameters of particles formed by forcing liquid through the vibrating piezoelectric plate is related to the diameters of the holes in the vibrating piezoelectric plate. Liquid particles (drops of the bulk liquid) are directed into a space filled with air which is inhaled by a patient or user for treatment.

Larger particles land on the tissues closest to the point of entry into the body because of their larger mass and inability to maintain entrainment in a flow of air as particles are inhaled. As particle sizes decrease, particles are better able to maintain entrainment in a flow of air as the particles are inhaled, traveling farther from their point of entry. As particles lose entrainment, the particles land on surfaces respiratory system, including the mouth, to perform a disinfecting function. The disinfection function is performed at locations where particles of ethyl alcohol solution land on the interior surfaces and maintain a concentration of ethyl alcohol above about 40%, as described above. A germicidal dose of ethyl alcohol solution is a quantity of ethyl alcohol solution delivered into the body to achieve a surface concentration of ethyl alcohol without dilution from adsorption of water from body tissues or exhalation.

Ranges of particle diameters for germicidal treatment are presented below. The particle diameter distributions presented below are not limiting. The ranges are flexible and deviations from the ranges indicate that the particle distribution pattern on interior body surfaces shifts according to the shift in particle diameter distribution. For purposes of the present discussion, large particles have a range of diameters of between about 50 μm (micrometers, or microns) and about 500 μm (or, 0.5 millimeters (mm)). Middle-sized particles have a range of diameters between about 10 μm and about 50 μm. Small particles have a range of diameters between about 5 μm and about 10 μm. Extra-small particles have a range of diameters between about 0.5 μm and about 5 μm. The extra-small particles are entrained with inhaled air into the alveoli in the lungs. The smallest size particles are so efficiently entrained that there is little impact on tissues in the mouth and in the portions of the respiratory system closest to the point of entry (e.g., the mouth or nose).

Particles having diameters in the extra-small range (e.g., between about 0.5 μm and about 5 μm) are absorbed through the alveoli directly into the bloodstream. A side effect of direct absorption of particles of ethyl alcohol solution through the alveoli is rapid intoxication, as described in U.S. patent application Ser. No. 16/230,992, titled "A METHOD OF DELIVERING ALCOHOL" and filed on Dec. 21, 2018. Rapid intoxication, or rapid brain effect, is a hallmark of alveolar absorption of ethyl alcohol absorbed directly into blood in the lungs flowing between the right ventricle and the left atrium.

Germicidal treatment of respiratory tissue surfaces carries some risk of intoxication, with decreasing risk for increasing particle diameters. Larger droplets of ethyl alcohol solution lose entrainment closer to the point of entry (e.g., the mouth or nose) and land on interior body surfaces, where the solution is absorbed into venous or arterial blood, or into body tissues, or into lymph. Absorption of ethyl alcohol solution into fluids or tissues other than blood in the lungs flowing between the right ventricle and the left atrium provides the body with a mechanism of metabolizing the ethyl alcohol slowly, without triggering the rapid intoxication effect referenced above, and without causing hangover after treatment (because the quantities of ethyl alcohol solution for germicidal treatment are quite small compared to amounts which cause hangover symptoms after drinking).

FIG. 1 is a flow diagram of a method 100 of disinfecting interior tissue surfaces of the upper or lower respiratory system, in accordance with some embodiments. Method 100 includes an operation 102, wherein a portion of the respiratory system is selected for treatment. For purposes of the present disclosure, the tissues of the upper respiratory system include the interior tissues surface of the nose, sinuses, throat, and mouth. For purposes of the present disclosure, the tissues of the lower respiratory system include the mouth, throat, and lungs. In embodiments of the method where the upper respiratory system is being treated, the method proceeds from operation 102 to operation 104. In embodiments of the method where the lower respiratory system is being treated, the method proceeds from operation 102 to operation 124.

In some embodiments, selecting a portion of the respiratory system for treatment further comprises selecting a nebulizer for treating the respiratory system, the nebulizer being configured to produce a plume of particles which will deposit on respiratory system tissues to perform the germicidal treatment. Once the selected portion of the respiratory system has been identified, the respiratory system tissues therein are targeted by selection of a nebulizer which generates particles that will deposit thereon.

Tissues of the upper respiratory system are treated by delivering a plume of particles from a nebulizer using a mask to direct particles into the nose during inhalation. Inhalation through the nose allows for droplets of ethyl alcohol solution to be deposited on the interior of the nose, sinuses, and throat as air passes through the nose and enters the lungs.

Tissues of the lower respiratory system are treated by delivering a plume of particles from a nebulizer using [1] a mask, as described above for nasal inhalation, and/or [2] a mouthpiece to direct particles into the mouth. Treatment of the lower respiratory system by delivery through the mouth is believed to be more efficient at delivering particles to the lungs because the pathway from the mouth to the lungs is more direct, with less opportunity for unintended particle deposition in the nose and sinuses during navigation of the nose and throat.

In an operation 104, a nebulizer with a mask is provided to a patient for treatment. In some embodiments, the nebulizer is a jet-type or pot-type nebulizer, which agitates a solution of ethyl alcohol (or other germicidal agent) and produces a mist or plume of particles for inhalation. In some embodiments, a jet-type or pot-type nebulizer has a well into which a solution is added, and the solution level is monitored to determine when a dose of solution has been delivered by the nebulizer. In some embodiments, the nebulizer is an active mesh nebulizer with a vibratable piezoelectric plate (e.g., the active mesh) configured to produce large particles, or large droplets, for treatment of the nasal passages, sinuses, and throat. Other types of nebulizers also fall within the scope of the present disclosure, provided the other types of nebulizers are able to produce particles in the diameter range described above for upper respiratory system treatment.

In an operation 106, a plume of particles is generated by the nebulizer for treatment. In embodiments of the method where a jet-type or pot-type nebulizer is provided to a patient, generating a plume of particles is done by, e.g., providing a stream of pressurized air through the liquid reservoir of a jet-type or pot-type nebulizer. In embodiments of the method where an active mesh nebulizer is used to generate the plume of particles (e.g., particles of the treating solution), the particles are generated by providing an electrical stimulus to the vibratable piezoelectric plate when the treating solution is directly against one side of the vibratable piezoelectric plate. In some embodiments, the plume of particles is a continuous plume (e.g., as with some jet-type or pot-type nebulizers, which are configured to generate a plume of particles of a solution in the pot or liquid reservoir for so long as the compressed gas is directed at the solution in the pot or liquid reservoir. In some embodiments, the plume of particles is a discontinuous plume (e.g., plume production is interrupted to provide a patient with time to retain a breath after inhalation, and to exhale, and to pause, according to a patient instruction or a programmed delay on the nebulizer, prior to a next inhalation of particles of treatment solution).

In an operation 108, the plume of particles is directed to the mask for inhalation by the patient. Directing the particles to the mask or inhalation is done by, e.g., connecting an exhaust or exit tube to the chamber where the plume of particles is generated (for a jet-type or pot-type nebulizer), or by directing the active mesh toward a volume surrounded by the mask when against the mask is against a patient's face.

In an operation 110, the patient inhales the particles through the nose. The inhalation rate for smaller particles is not related to the effectiveness of the germicidal treatment because the particles are efficiently engrained by the inhaled air and travel into the lungs before the particles fall out of the airstream and deposit on lung tissue surfaces. The inhalation rate for larger particles is somewhat related to the effectiveness of germicidal treatment of upper respiratory system tissues because large particles deposited more quickly than smaller tissues. Rapid deposition of large amounts of ethyl alcohol in nasal passages or the throat causes irritation under some circumstances, resulting in sneezing or coughing, which expels the solution during treatment. Thus, for treatment with nebulizers which produce larger particles, slow or short inhalations are recommended for more effective treatment. Further, with slow or short inhalations (e.g. lasting up to about 8-10 seconds for a full inhalation), the breath may be paused or interrupted when a patient feels irritation, avoiding expulsion of the treating solution. With slow or short inhalations, the patient is also able to sense the deposition of the droplets of treating solution on tissues (e.g., by feeling the tissues become cool, or responding to the ethyl alcohol) and regulate the inhalation to adjust the distribution of treating solution particles on tissue surfaces. In some embodiments, inhalation speed is increased or decreased by a patient in order to adjust the distribution of treating solution particles. In some embodiments, a duration of inhalation is increased or decreased to adjust the distribution or load on the respiratory system tissue of the inhaled particles of treating solution.

In an operation 112, the patient retains the breath. Retaining the breath in the lungs allows the treating solution droplets to land on the interior surfaces, to disperse across the interior surfaces, and perform the germicidal function. In some embodiments, retaining the breath is recommended to help a patient avoid coughing or sneezing due to irritation, thus promoting the germicidal treatment. In some embodiments, the breath is retained for a period of 3-10 seconds. Retaining the breath for less than 3 seconds is likely to result in exhalation of particles of treating solution without deposition on the tissue surfaces. Retaining the breath for more than 10 seconds is likely to result in a patient triggering a cough reflex under some circumstances (e.g., with post nasal drip or other throat irritation which occurs or is exacerbated with deposition of treating solution on throat tissues).

In an operation 114, the patient exhales the breath. Exhalation is through either the nose or mouth. Exhalation through the mouth is believed to be slightly more efficient for germicidal treatment of the upper respiratory system because there is less opportunity for evaporation of the deposited ethyl alcohol solution. The change in effective germicidal treatment due to exhalation through the mouth versus exhalation through the nose is believed to be due to the different amounts of evaporation which occur after disinfection of interior tissue surfaces and evaporation of ethyl alcohol from the interior tissue surfaces. According to theory and belief, the change in effective germicidal treatment is small.

In an operation 116, a determination is made as to whether a dose of ethyl alcohol solution has been delivered to the patient. For treatment of the upper respiratory system, if a dose of ethyl alcohol has not been delivered to the patient, the method proceeds to operation 106 and operations 106-114 repeat until the dose has been delivered.

In operation 116, a size of the dose of ethyl alcohol solution (treating solution) is related to the part of the respiratory system being treated. Doses for upper respiratory system treatment are larger than doses for lower respiratory system treatment. In an embodiment, a dose for treating the upper respiratory system of a patient using a nebulizer which produces a continuous plume of particles ranges from about 1.5 to about 2 mL of ethyl alcohol solution, and includes a buffer amount of solution to compensate for plume production during times the patient retains an inhaled breath, and during times that the patient is exhaling.

In an operation 126, a plume of particles is generated by the nebulizer for treatment. In some embodiments, generating a plume of particles for treatment of tissues of the lower respiratory system is done by activating an active mesh nebulizer or other type of nebulizer configured to make particles smaller than about 50 µm. For further information regarding the generating plumes of particles, refer to U.S. patent application Ser. No. 16/836,485, titled "NEBULIZER FOR TIME-REGULATED DELIVERY" and filed on Mar. 31, 2020, incorporated herein by reference.

In an operation 128, the plume of particles is directed to the mouthpiece. Directing the plume of particles into a mouthpiece using an active mesh nebulizer includes fitting a mouthpiece over the vibratable piezoelectric plate in the active mesh nebulizer to form a retaining volume around the side of the vibratable piezoelectric plate below which particles form when the plate vibrates. Particles are retained in the retaining volume to allow air inhaled through e.g. holes in the sides of the sides of the mouthpiece to carries particles into the lungs during inhalation.

In an operation 130, the plume of particles is inhaled through the mouth, entrained with the air inhaled through holes in the mouthpiece to carry the particles into the lower respiratory system.

In an operation 132, the patient retains the breath. Retaining the breath in the lungs allows the ethyl alcohol droplets to land on interior surfaces, to disperse across the interior surfaces, and perform the germicidal function. In some embodiments, repeated plume inhalation builds up the concentration of ethyl alcohol solution on the interior surfaces to achieve the germicidal treatment results.

In an operation 134, the patient exhales the breath. Exhalation is through the nose or the mouth. After operation 134, the method 100 proceeds to operation 116.

In an operation 116, a determination is made as to whether a dose of ethyl alcohol solution has been delivered to the patient. For treatment of the lower respiratory system, the method proceeds to operation 126 and operations 126-134 repeat until the dose of medication has been delivered.

In some embodiments, a dose for treating the lower respiratory system of a patient using an active mesh nebulizer ranges from 0.1 ml to 0.5 ml, and does not include a buffer amount of solution to compensate for continuous plume production during retention of a breath, or exhalation. In some embodiments, the active mesh nebulizer is configured to deliver a time-regulated series of plumes of particles to an individual on sequential inhalations in order to reduce a total amount of medication delivered while having precise control over the dose delivered. In some embodiments, the vibratable piezoelectric plate activates a single time and a patient receives a single plume of particles from a nebulizer, and the nebulizer shuts off until time for a subsequent treatment. In some embodiments, the vibratable piezoelectric plate activates between 2 and 5 times, and the patient receives between 2 and 5 plumes of particles on different inhalations, and then halts until time for a subsequent treatment. In embodiments with larger doses, the vibratable piezoelectric plate halts between times of delivering portions of the dose of treating solution to the patient. Halting vibratable piezoelectric plate reduces wasted medication (the treating solution).

On completion of operation 116, the method continues to operation 118, wherein the nebulizer (with mask or mouthpiece) is removed at the end of respiratory system treatment.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The use of an active mesh nebulizer with lockout bar coded capsules/cartridges to help aid most consequences of alcohol use syndrome. Capsules coded with a bar code or other identifying mark (e.g., a QR code) or electronic identifier (radio frequency identifier-RFID) is used to regulate access by the nebulizer to a solution to be nebulized. In some embodiments of the nebulizer, a capsule (or, cartridge) containing ethyl alcohol or an ethyl alcohol solution is a single-use capsule. In some embodiments, the capsule or cartridge has a liquid fill volume of at least 0.5 milliliters and not more than 10 milliliters. In some instances, the liquid fill volume of a capsule or cartridge ranges from at least 1 ml to not more than 5 ml. In a preferred embodiment, the capsule has a liquid fill volume of about 4 ml. A fill volume greater than about 10 ml is inconvenient to carry because of the size of the capsule, and a difficulty of extracting liquid from the capsule after more than 70% of the fluid located therein has been volatilized. At liquid fill volumes less than 0.5 ml, the surface tension of the fluid in the capsule draws a majority of the fluid against the metal mesh that volatilizes the liquid, making regulation of fluid level difficult to manage. Thus, a minor child or a person who does not own a nebulizer is restricted from using the nebulizer against a predetermined usage plan. A lock out barcoded capsule containing ethyl alcohol, tethered to a smartphone application that regulates operation of an active mesh nebulizer, prevents unauthorized use by non-designated users of the active mesh nebulizer, and/or excessive use, misuse, or abuse by a designated user.

Annually in the United States, approximately 88,000 deaths are associated with consequences of alcohol consumption. According to the National Institute of Health (NIH) 2016 statistics, excluding traffic deaths of approximately 10,000 persons, 62,000 men and 26,000 women die from alcohol-related conditions. Liver deaths affect approximately 21,815 persons. Other alcohol-related deaths affect about 34,865 persons, including cancer deaths associated with alcohol use include mouth, tongue, esophagus, pancreas, stomach, colon and breast. Fetal alcohol syndrome is found in $\frac{1}{100}$ births or about 44,000 annually. Fetal alcohol syndrome is life long and has no known antidote as of 2018.

According to present theory and belief, delivery of volatilized ethyl alcohol (pure, or in a solution) to the brain via nebulized (as described hereinbelow) particles absorbed through the alveoli produces a brain effect ("buzz" or "intoxication") within 60 seconds without production of alcohol-related metabolites that induce hangover symptoms (also called "body effects", which may include some brain-related symptoms). In some embodiments, delivery of ethyl alcohol produces onset of a brain effect within 10 seconds. In some embodiments, cessation of a brain effect occurs rapidly, with no protracted or elongated recovery period (e.g. a recovery period in which residual ethyl alcohol in a person causes decreased coordination or cognition, while the euphoric portion of a brain effect has ceased).

Ethyl alcohol is an amphiphilic molecule, with a hydrophilic portion (the hydroxyl (—OH) functional group) and a hydrophobic portion) the ethyl (—$C_2H_5$) moiety. The brain is known to have a large proportion of fat or aliphatic molecules located therein. Ethyl alcohol rapidly printed traits the brain blood barrier such that brain tissue rapidly absorbs ethyl alcohol from the bloodstream.

Ethyl alcohol is added to the bloodstream by using an active mesh nebulizer to generate small particles of ethyl alcohol solution in a stream of air inhaled into the lungs during respiration. As described hereinabove by reference, small particles of ethyl alcohol solution produced by an active mesh nebulizer have a size between 0.5 and 5 micrometers (μm) in diameter. Small particles having a size between 0.5 and 5 μm enter alveoli in the lungs rapidly, and have a high residence time within the alveoli before being absorbed into the bloodstream.

Particles with a diameter greater than 10 μm adhere to tissues in the nose and throat. Particles with a diameter smaller than 10 μm are inhalable (enter the lungs) without being trapped on surfaces or tissues in the nose and throat. Particles with diameters smaller than about 5 μm are respirable, or able to penetrate deep into the lungs. Thus, droplets of alcohol solution having a diameter ranging between 0.5 and 5 μm are able to penetrate deep into the lungs, and coat inner surfaces of the tracheobronchial regions. Because alveoli contain thin membranes through which gasses are exchanged between the blood and air within the lungs, particles or liquid droplets which enter alveoli have an effect on respiration rates and health. Ethyl alcohol solution droplets in the alveoli are readily absorbed by the blood by directly crossing the alveoli membrane.

Venous blood from the body and brain enters the right atrium of the heart. The right atrium pumps venous blood into the right ventricle, from which the venous blood is pumped into the lungs for oxygenation. Oxygenated blood received from the lungs enters the left atrium of the heart. The left atrium pumps oxygenated blood into the left ventricle, from which oxygenated blood is pumped out of the heart and to the body. Alcohol absorbed directly into the blood from alveoli of the lungs passes through the left atrium and the left ventricle before flowing to the remainder of the body.

Approximately 20% of the blood flowing from the heart is pumped directly to the brain. Blood exiting the heart from left ventricle returns to the heart within about one minute. Thus, approximately 20% of alcohol directly absorbed into the blood from the lungs travels to the brain within 60 seconds of uptake in the lungs.

Because ethyl alcohol has a lipophilic (or, hydrophobic) ethyl moiety, ethyl alcohol is readily taken up by fat in brain tissue. Thus, delivery of nebulized ethyl alcohol using an active mesh nebulizer as described hereinabove by reference produces a brain effect, whether a "buzz" or intoxication, for small volumes of alcohol solution being nebulized.

FIG. 2 is a flow diagram of a method 200 of delivering ethyl alcohol during respiration without significant body effects, according to an embodiment. In an operation 205, a nebulizer has a control system that is evaluated to determine whether an operational limit of the nebulizer has been exceeded. And operational limits of an active mesh nebulizer includes one or more of a measured volume of delivered alcohol solution, an elapsed time between delivery sessions of alcohol from the active mesh nebulizer, a calculated blood-alcohol content of a nebulizer user, a match between an identifier associated with a capsule or cartridge fitted onto an active mesh nebulizer at the start of an operational period, and an identifier associated with the capsule or cartridge at a later time when a nebulizer airstream is requested, and/or an elapsed time over which a predetermined volume of alcohol solution has been delivered by the active mesh nebulizer.

From operation 205, when an operation limit has not been exceeded, the method continues with operation 210. From operation 205, when an operation limit is exceeded, the method continues with operation 240.

In operation 210, a surface of an ethyl alcohol solution is positioned in contact with an active mesh of a nebulizer, according to some embodiments. As described herein, and active mesh nebulizer includes a vibrating metal mesh withholds situated therein. When a solution service is in contact with the vibrating metal mesh, and the vibrating metal mesh is activated to vibrate at high velocity, droplets of solution are generated above the metal mesh. A quantity of droplets of solution is regulated by controlling a duration of metal mesh vibration. A greater quantity of droplets is provided by the active mesh nebulizer with a longer vibration time, according to either a predetermined vibration time programmed into the active mesh nebulizer, or according to a user requested vibration time.

In an operation 215, the active mesh nebulizer performs a cleaning step, in which the vibrating mesh vibrates while not in contact with a solution situated in a capsule attached to the active mesh nebulizer. Operation 215 is an optional operation. In some embodiments, operation 215 occurs after an elapsed time after capsule placement within the active mesh nebulizer has occurred in order to reduce a quantity of contaminants in a stream of particles generated by the active mesh nebulizer. Particles include, in some embodiments, portions of biofilm or bacterial contamination present within the active mesh nebulizer. Bacterial contamination or biofilm forms within a nebulizer as a function of suitable growing conditions within a favorable range of temperature and humidity for growth of contaminating organisms. A lock-out bar-coded capsule reduces growth of bacterial contamination and biofilms by preventing cross-contamination of a nebulizer from multiple capsules.

In an operation 220, an active mesh nebulizer determines whether or not inhalation is occurring. When inhalation occurs, the method continues with operation 225. When inhalation is not occurring, method 200 continues with operation 222 wherein the nebulizer performs a wait operation. Operation 222 has a duration that is preprogrammed into the nebulizer, or is modified by a user, according to some embodiments. For example, in a non-limiting embodiment of the method, operation 222 continues for 0.5 seconds, after which method 200 continues to operation 220. Upper time for wait time (5 or 10 seconds).

In operation 225, an active mesh nebulizer performs a volatilization step, in which the vibrating mesh begins high-frequency motion against a surface of the solution located in the nebulizer capsule to generate a stream of particles. In operation 230, the stream of particles is added to a flow of air during the inhalation process. According to some embodiments, operation 225 occurs before operation 220. In a preferred embodiment, operation 225 occurs after operation 220 has been performed. In operation 235, the volatilization process ends as the metal mesh vibration is halted. From operation 235, method 200 continues to operation 205, wherein the nebulizer determines whether an operation limit of the nebulizer has been exceeded.

In operation 240, nebulizer operation halts. Method 200 proceeds from operation 205 to operation 240 when a sufficient quantity of particles has been delivered (e.g., the operation limit of sufficient particle quantity has been exceeded).

In some embodiments, a minor brain effect, or buzz, is generated by nebulization and delivery of 2 milliliters (mL) of ethyl alcohol solution having 40% of ethyl alcohol and 60% water. In some embodiments, a major brain effect, or intoxication, is generated by nebulization of 2 mL of ethyl alcohol solution having 60% ethyl alcohol and 40% water. An active mesh nebulizer is configured to nebulize an ethyl alcohol-containing solution ranging from about 1% up to 100% ethyl alcohol. It is noted, however, that the degree a brain effect of ethyl alcohol solution delivered by nebulization is affected by body mass of an individual, gender of the individual, personal tolerance of alcohol delivery, and body composition of the individual, among other factors. Thus, individual brain effects resulting from delivery of nebulae stuff alcohol solutions using an active mesh nebulizer as described hereinabove are highly variable, but the general principle of rapid occurrence of a brain effect caused by nebulization should be understood to be a result of the particle size of ethyl alcohol solution droplets generated by the active mesh nebulizer and the rapid uptake of ethyl alcohol by blood solution in the lungs after respiration of said particles.

A relevant feature of delivery of ethyl alcohol solution particles to the lung by an active mesh nebulizer is that the brain affect caused by the absorbed of alcohol has a rapid onset, but is not followed by deleterious effects of intoxication when the brain effect ceases. The small volume of alcohol solution delivered to the bloodstream through the lungs by the active mesh nebulizer induces rapid brain affect because a significant portion (approximately 20%) of the absorbed alcohol travels directly to the brain. The remaining volume of alcohol not delivered directly to the brain (approximately 80%) circulates the remainder of the body. Some or all of the remaining volume of alcohol is absorbed by other body tissues, including the liver. An amount of alcohol dehydrogenase located in the liver is sufficient to receive and metabolize alcohol received an absorbed by the liver, producing known and recognized alcohol metabolic byproducts, including acetaldehyde. It is of note, however, that the amount of acetaldehyde and other alcohol metabolic byproducts, is greatly reduced with respect to traditional alcohol consumption techniques, drinking and absorption of the alcohol through the stomach and small intestine.

The onset of brain effect after delivery of volatilized ethyl alcohol solution occurs within 60 seconds. In some embodiments, the onset of brain effect occurs within 10 seconds of the initial delivery of volatilized ethyl alcohol. Onset of a brain effect occurs after volatilization (or, nebulization) of less than 0.5 ml ethyl alcohol solution. Thus, a quantity of ethyl alcohol in the blood is below a detection threshold of a blood alcohol content (BAC) blood test, or a test that monitors alcohol vapor upon breathing through a test apparatus (e.g., a "breathalyzer" test).

Ethyl alcohol produces a brain effect by disrupting neurotransmitter production. Brain effects from ethyl alcohol continue for approximately as long as a concentration of ethyl alcohol in the brain exceeds an intoxication threshold. Once a concentration of ethyl alcohol in the brain falls below the intoxication threshold, the neurotransmitter disrupting effects of ethyl alcohol cease and the brain effect is no longer experienced. Thus, according to current theory and belief, cessation of a brain effect of ethyl alcohol occurs rapidly (e.g., within less than about 10 minutes from an "effected" state as the brain tissues metabolizes ethyl alcohol absorbed by brain tissue. Because there is no "reservoir" of unabsorbed or unmetabolized alcohol in the stomach, intestine, blood, or other body tissues, the brain effect of alcohol ceases rapidly, as described above. Thus, after an abbreviated recovery period following cessation of brain effect subsequent to delivery of alcohol to brain tissue using an active mesh nebulizer, there is no residual mental incapacitation or adverse effect on cognitive ability. In some embodiments, rapid cessation of brain effect includes rapid return of physical coordination and/or motor skills. Thus, when a subject has received an ethyl alcohol delivery by means of an active mesh nebulizer as described hereinabove, upon cessation of the euphoric brain effect and the abbreviated recovery period, there is no residual deleterious cognitive effect or adverse impact on coordination or motor skills. Rather, a subject returns to a fully sober state extremely rapidly. According to theory and belief, the abbreviated recovery period for a return to full sobriety is not less than around 1 minute, and not greater than about 20 minutes, according to an amount of delivered ethyl alcohol. In some embodiments, the recovery period for a return to full sobriety subsequent to cessation of euphoric brain effect is between about 5 and about 10 minutes. Thus a subject, having received a delivery of nebulized (or volatilized) ethyl alcohol as described herein by an active mesh nebulizer, is able to, e.g., operate a motor vehicle or perform cognitively demanding operations in a manner consistent with the subject's pre-delivery capacity immediately after the recovery period after cessation of the euphoric brain effect. When the cessation of brain effect occurs, in some instances the recovery period is immediate (less than one minute). When the brain effect ends, because there is such a small amount of alcohol present in the brain and body of a person to whom the alcohol has been delivered, the common physical consequences of intoxication or drunkenness are less likely to occur. Consequences such as dizziness, falling, automobile accidents, and so forth are reduced and/or eliminated because the balance and coordination of a person with alcohol in the brain is impacted by the brain alcohol content. When the alcohol content in the brain drops below a threshold level, the physical coordination and balance return rapidly and the consequences of falling (sprains, bone breakage, concussion, torn muscle or ligament/tendon) are reduced or eliminated because the person is readily aware of the return of sobriety and mental clarity to the person.

Some aspects of the present disclosure relate to a method of delivering alcohol to a person with a brain effect (euphoria, and so forth) with a blood alcohol limit that is less than 0.02% and more than 0.0001%.

While the brain affect caused by nebulization of ethyl alcohol solutions occurs quickly, and with relatively small volume of nebulized ethyl alcohol solutions, body effects of alcohol consumption are reduced and/or eliminated. Short-term body effects include "hangover" symptoms, such as fatigue, weakness, excessive thirst, headaches, muscle aches, nausea, and vomiting. Other "hangover" symptoms include dizziness, sleep disruption, sensitivity to light and sound, and shakiness. Long-term body effects of alcohol consumption include damage to the gastrointestinal tract, liver cirrhosis, heart damage, elevated triglyceride levels, fat buildup in the liver, and pancreatitis. Long-term body effects of alcohol consumption also include elevated cancer risks as described above. Further, fetal alcohol syndrome is associated with alcohol consumption during pregnancy with life-long effects on cognitive function and physical coordination of the child.

According to present theory and understanding, delivery of alcohol by means of an active mesh nebulizer produces rapid brain affect and little or no short term body affects. In some instances, delivery of alcohol using an active message nebulizer produces mild and or pronounced brain effects with no "hangover" symptoms when the brain effective alcohol delivery ends.

As described previously, active mesh nebulizers neither heat nor boil liquids located therein. Rather, active mesh nebulizers contain a metallic grid with numerous small diameter holes located therein. The metallic grid is placed in contact with liquid within the nebulizer, after which the grid is rapidly vibrated to generate particles and liquid with diameters as described hereinabove. Some embodiments of active mesh nebulizers include grids containing thousands of perforations or holes, wherein said grids are made of piezo-electric materials that oscillate upon electrical stimulation.

One feature of active mesh nebulizers is that metallic grid self cleans upon vibration of the grid. Particles, liquids, or films coding the grid are vibrated off of a metallic grid surface when the grid is vibrated for extended periods (e.g., vibrational periods lasting three seconds or longer). Thus, each operation of a metallic grid to generate droplets of solution can include, according to some embodiments, an initial cleaning phase, and a droplet formation phase after the cleaning phase. By dividing metallic grid operation into two phases, the stream of particles generated by the active mesh nebulizer to be delivered into the lung for uptake by the blood has a reduced incidence of bacterial or other contaminants, as compared to nebulizers that generate droplets using methods other than vibrating metallic grids.

According to present theory and understanding, delivery of alcohol by means of an active mesh nebulizer provides a user an opportunity to consume alcohol with brain effect and also provide other body tissues, including heart, gastrointestinal tract, liver, bladder, and so forth, opportunity to heal from previously incurred tissue damage caused by alcohol consumption. For example, a patient in a rehabilitation facility is able to receive delivered alcohol in quantities configured to achieve brain effect during addiction treatment without incurring additional tissue damage. Thus, symptoms of alcohol withdrawal are minimized during a alcohol addiction treatment process, without incurring further gross bodily damage associated with large quantities of alcohol commonly associated with drinking. For example, symptoms of alcohol withdrawal include (for mild severity): anxiety, insomnia, nausea, and abdominal pain; (for moderate severity) elevated blood pressure, elevated body temperature, heart rate variation, mental confusion; and (for high severity) hallucinations, fever, seizures (delerium tremors), and/or agitation. Alcohol delivery via the lungs and absorption through the blood to moderate withdrawal symptoms occurs for periods up to 10 days in order to regulate withdrawal symptoms without inducing additional addictive behaviors or additional tissue damage by a patient undergoing withdrawal therapy and assistance. Timing and dosage of alcohol delivery using volatilized droplets, as described hereinabove, are determined according to a patient response to alcohol delivery, a patient tolerance to alcohol, and severity and type of symptoms experienced by a patient.

According to present theory and understanding, a person without any alcohol-related tissue damage (e.g., in the gastro-intestinal tract, liver, or cancer symptoms) experiences delivery of alcohol to the brain by means of an active mesh nebulizer to achieve a euphoric brain effect with no, or only minor, tissue damage or alcohol toxicity-related symptoms associated with consumption of large amounts of alcohol. The benefit to a user is that euphoric effects are experienced with little, or no, gross tissue damage or increased cancer risk associated with alcohol consumption.

A further aspect of the present disclosure is an increased degree of accuracy in alcohol delivery to a user, or accurately titrate the central nervous system. Because an active mesh nebulizer is capable of quantifying an amount of alcohol solution delivered to a use (by, for example, monitoring a time period during which the active mesh vibrates to generate a particle stream, and/or by monitoring a remaining level of alcohol solution within the nebulizer), the user is able to monitor and regulate alcohol consumption with greater precision than by drinking alcohol. Further, some embodiments of an active mesh nebulizer are programmed to deliver a predetermined amount of alcohol to a user before halting further delivery to allow a user to recover from the brain affect before further delivery of nebulized particles occurs.

The use of this nebulizer will allow the individual to accurately titrate their central nervous system effect as previously described. Some embodiments of an active mesh nebulizer are configured to adjust generation and delivery of nebulized ethyl alcohol solution to a user by pre-programming the active mesh nebulizer with a set of user parameters. These parameters include, in some embodiments, body mass, gender, body composition, desired level of brain effect (determined empirically and provided by a user), and so forth. Some embodiments of active mesh nebulizers include a performance lockout system figured to recognize a concentration of ethyl alcohol in a solution contained in a nebulizer capsule. Some embodiments of active mesh nebulizers include a performance lockout system that halts further droplet production when a nebulizer capsule is removed from the nebulizer and a new nebulizer capsule is added to the nebulizer. Nebulizer capsules include, in some embodiments, barcodes or other identification means configured to provide a nebulizer with capsule content information.

Long-term body effects of alcohol consumption, including effects on peripheral nerves, the liver, and gastrointestinal tract, are largely dependent on the dose, or quantity of alcohol consumed by an individual. The higher the concentration of alcohol in the blood, or blood-alcohol content, and the longer period of time alcohol is consumed, the greater the damage that is likely to occur to an individual. Despite individual variations regarding tolerance of alcohol exposure, where some individuals experience harm and some do not at the same level of acute or chronic exposure, tissue damage generally follows long term exposure and high levels of exposure to ingested alcohol. Alcohol delivery through the lung by means of small (0.5-5 micrometer) droplets reduces the overall exposure of body tissues to ethyl alcohol while providing similar (e.g., euphoric) brain effects with greatly reduced risk of developing illness or tissue damage associated with long-term alcohol exposure. There is no known dose/consequence relationship.

This application describes the use of an active mesh nebulizer which produces very small particles (1-5 micron) of ethyl alcohol in various concentrations to produce an easily titrated effect and avoid damage to the liver, gastrointestinal tract or peripheral nervous system. This effect is short lived (30 minutes to 2 or more hours) and allows tissues already damaged by alcohol abuse to heal. It also avoids central nervous system alcohol withdrawal and could be useful to treat hangovers in some individuals. According to theory and belief, the effect occurs by receptor site saturation in the brain even at low total blood serum levels of ethyl alcohol. A single use lock out barcoded capsule/cartridge containing ethyl alcohol in various concentrations along with a tethered smartphone application prevents unauthorized use by others as well.

Alcohol is a very small molecule which has the unusual property of being both hydrophilic and lipophilic. Alcohol enters the brain by two pathways. First, Filtration which allows alcohol to move through the water spaces because it dissolves in water. Second, passive diffusion due to the lipophilic nature of ethanol. This allows it to move without transport molecules across cell membranes and into the brain.

Other small lipophilic molecules can also move passively across the blood brain barrier. These include nicotine, marijuana, heroin, fentanyl, and other opioids, all have a significant brain effects. Glucose and vitamins are carried across the blood brain barrier by transport molecules and this process is known as active transportation and requires energy expenditure not seen with lipophilic compounds such as alcohol.

Ingested alcohol is metabolized in the liver by alcohol dehydrogenase to produce acetaldehyde which is the molecule that causes nausea, headache, fatigue and other toxic side effects recognized in the hangover syndrome.

Our device which uses much smaller amounts of ethanol and bypasses the liver largely avoids the toxic side effects of acetaldehyde as only very small amounts of alcohol dehydrogenase would be needed to eliminate it from the brain. Additionally, acetaldehyde has been implicated as the responsible agent in the relationship between alcohol consumption and increased cancer risk.

In a medical setting, nebulizers are used to deliver pharmacological compounds to medical patients for treatment of medical conditions. Nebulizers are also used to deliver non-medical products to persons in non-medical settings, such as nicotine to persons in nicotine-replacement therapy. However, previous nebulizers, including aerosol, passive mesh, and active mesh nebulizers, exhibit imprecise dosage control of the pharmacological compound being supplied to the patient. In many instances, nebulizers volatilize a solution having one or more pharmacological compounds into droplets and the dosing of the patient or user is regulated by the amount of time that the user spends inhaling the stream of particles or droplets, and/or the efficiency with which the stream of particles or droplets is directed toward the patient or user's nose or mouth to be inhaled. In many situations, patients are treated with incorrect dosage of a pharmacological compound in order to achieve a rapid response in the patient's body, which sometimes results in side effects from the over dosage of the pharmacological compound.

Treatment of a patient or user with open cup nebulizers involves placing a solution of the pharmacological compound in a bowl or cup, directing a flow of air through the solution to generate particles or droplets of the solution, and the flow of air directs the particles or droplets toward the patient or user's nose and/or mouth for inhalation. Open cup nebulizers produce a constant stream of particles or droplets which are inhaled at will by the patient or user.

HFA (hydrofluoroalkane) inhalers provide a more accurate dosage regimen than open cup nebulizers for a patient or user, where a pharmacological compound in suspension and a propellant are expelled from an inhaler mouthpiece in a high velocity stream of liquid and expanding gas into a patient or user's mouth during an inhalation. HFA inhalers do not reliably provide accurate dosages of pharmacological compounds to a patient or user. When a patient does not agitate the suspension of pharmacological compound in the HFA inhaler, the amount of pharmacological compound delivered to a user in a metered spray is below an anticipated level of the pharmacological compound because of insufficient mixing. Also, the direction of a stream of suspension into the patient or user's mouth is difficult to control. When the stream strikes the tongue, cheeks, or throat of the patient or user, the liquid tends to adhere to the tissue rather than continue into the lungs, reducing the effectiveness of dosing a medical condition with HFA inhalers. Patients or users also tend to cough when the suspension strikes the upper portions of the respiratory tract, expelling some of the suspension and further reducing the amount of pharmacological compound retained or absorbed by a patient or user. Thus, accurate dosage of medical conditions with HFA inhalers is difficult to coordinate. One or more embodiments of the present disclosure describe an active mesh nebulizer configured to provide accurate dosing of solutions of pharmacological compounds to patients or users.

Figure 3:
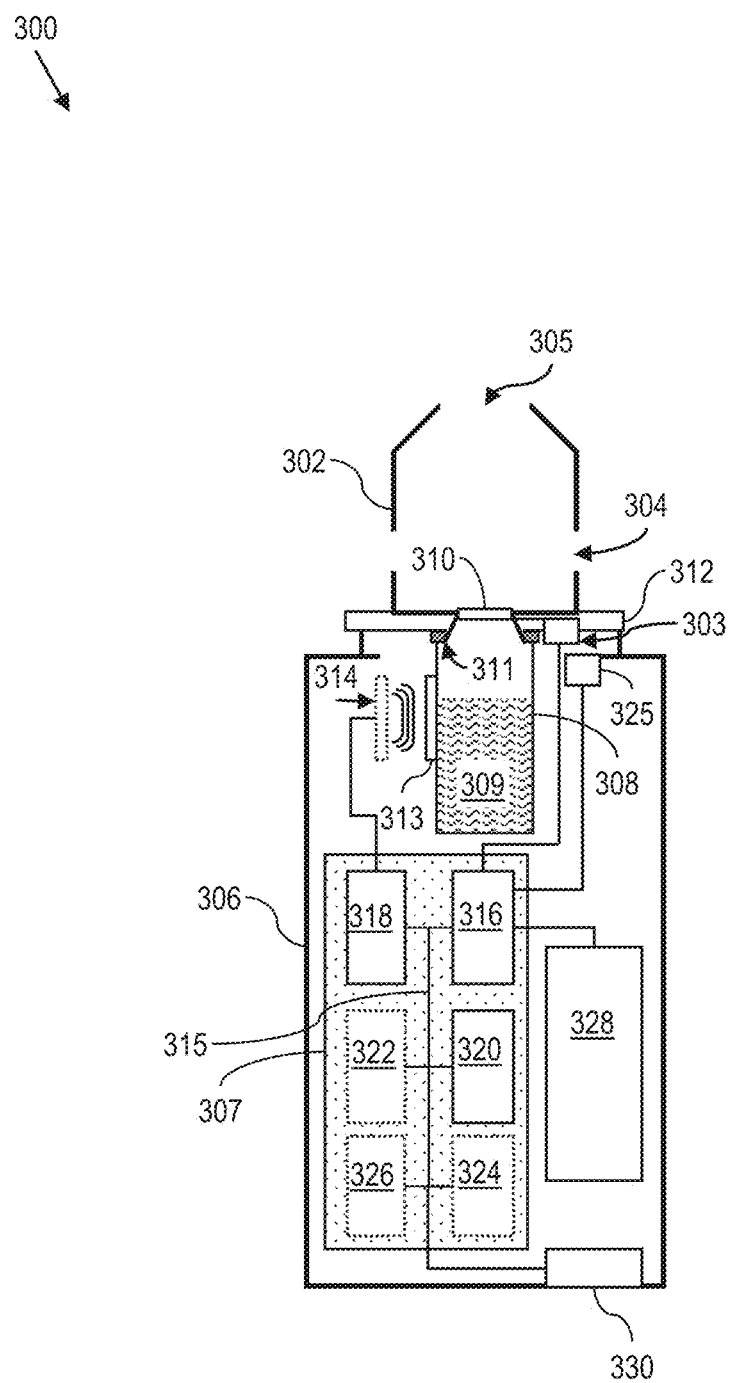
FIG. 3 is a schematic diagram of an active mesh nebulizer, in accordance with some embodiments.

FIG. 3 is a schematic diagram of an active mesh nebulizer 300, in accordance with some embodiments. An active mesh nebulizer is a nebulizer which produces a plume of particles or small droplets by causing a metal plate (active mesh 310) The active mesh nebulizer 300 includes a mouthpiece 302 with at least one hole 304 therein to allow air to enter the mouthpiece during a patient inhalation during operation of the active mesh nebulizer to produce a plume of particles (droplets) to treat a patient medical condition. In at least some embodiments, the at least one hole 304 is positioned on a side of the mouthpiece 302 and is configured to direct entering air toward the plume of particles and promote particle transport through a mouthpiece opening 305 and thereby into the patient's lungs. The mouthpiece 302 fits against a nebulizer body 306.

In some embodiments, a sensor 325 is in the nebulizer 300 to detect the mouthpiece 302 being against the nebulizer body, and/or the closure of the nebulizer body 306 with a vial 308 located therein. In some embodiments, the nebulizer body 306 and mouthpiece 302 are integral, and the vial 308 is added to the nebulizer from an opening in the nebulizer body, where a sensor monitors the body closure. The sensor is configured to monitor when the nebulizer body is opened and/or closed to ensure that the vial 308 containing a solution of pharmacological compound is not removed, substituted, or tampered with. Such monitoring, and ensuring that the vial assembly is not removed, substituted, or tampered with, is one aspect of securely providing pharmacological compounds to patients or users within medically acceptable dosing limits. Adulteration of pharmacological compound solutions is to be avoided because the nebulizer disclosed herein is more efficient than other approaches at providing pharmacological compounds to users via inhalation of plumes of particles or droplets. In some embodiments, the vial is made of glass in order to safely hold pharmaceutical compounds or medicinal compounds. In some embodiments, the vial is made of an organic or polymeric material. An organic or polymeric material is suitable for holding compounds that are for purposes other than treating medical conditions.

An active mesh 310 produces a plume of particles or droplets (not shown) that is directed toward a patient or user's lungs during inhalation by the user. Active mesh 310 is configured to produce particles having a diameter of not greater than 10 micrometers (μm). In some embodiments, more than 99% of the particles (or droplets) of solution in a vial in the nebulizer produced by the active mesh 310 have a mean particle diameter of 10 micrometers or less (see FIG. 4). In some embodiments, more than 95% of the particles or droplets produced by the active mesh 310 have a mean particle diameter of 5 micrometers or less. The subject matter of the present disclosure is extendable to nebulizers that produce plumes of particles or droplets with a wide range of particle distributions that also produce particles having diameters below 10 micrometers. An active mesh nebulizer produces, from a solution in the vial of the nebulizer, a plume of particles as a result of the mesh vibration, rather than by heating or boiling the solution. Thus, there is no contamination of the solution with mesh material, as occurs when a metallic heating element is used to elevate the temperature of a solution to produce vapor or streams of particles (e.g., in many e-cigarette devices). Further, by producing a plume of particles without heating or boiling the solution, there are no chemical changes to the pharmacological compounds of the solution because of elevated temperature during delivery to a patient or user.

The ability of particles to penetrate into the lungs and be absorbed by the body is a function of the size of the particles and the respiratory pattern of the user. Inhaled particles having a diameter greater than about 15 micrometers penetrate into the lungs as far as the bronchi because the cilia of the lungs capture the inhalable particles from further travel into the lung volume. Some small amount of the particles are absorbed, while most particles are cleared by the cilia and swallowed by the user after inhalation. Thoracic particles, ranging in size from 10 to 15 micrometers, penetrate into terminal bronchioles in the lungs. Particles ranging in size from 0.1 to about 6 micrometers are able to penetrate into the alveoli in the lungs and are readily absorbed through the alveoli into the circulatory system and body tissues. Particles that are unable to penetrate into the alveoli are absorbed into lung tissue and into the bloodstream with lower efficiency than particles that reach the alveoli and which are absorbed directly into the bloodstream across alveolar membranes.

Open pot nebulizers do not provide accurate doses because the patient inhalation time and volume of inhaled pharmaceutical product is extremely variable, depending on a patient's choice for inhalation duration and the amount of leakage of particles outside of the patient's mouth.

The absorption of the plume of particles or droplets increases when a patient or user of an active mesh nebulizer employs deep, slow inhalation for entrainment of the particles or droplets into alveolar spaces of the lungs. In some embodiments, the patient or user performs an inspiratory action over the course of 2-8 seconds and holds the inspired particles or droplets within the lungs to further promote absorption of the particles. In a preferred embodiment, the inhalation period or inspiratory action lasts between 3 and 6 seconds. In a preferred embodiment, the patient or user holds the plume of particles in the lungs for at least 5 seconds before an exhalation of the air from the lungs. According to an embodiment, the pause between inspiratory actions (and corresponding plume generation) is regular and even. In some embodiments, the patient or user regulates the duration of the pause between inspiratory actions and/or plume generation. In some embodiments, the duration of the pause between inspiratory actions and/or plume generation is regulated by the nebulizer, or by a third party such as a health-care professional that programs the nebulizer.

Active mesh 310 produces a plume of particles by vibrating at high frequency to trigger particle, or droplet, formation from a liquid against an inner surface of the mesh (e.g., the side facing the interior of the vial in the vial 308) on an outer surface of the mesh (e.g., the side facing the mouthpiece interior volume and mouthpiece opening). Active mesh 310 is a metallic disc having openings extending through the planar surface of the disc, such that the metallic disc, when electrically stimulated to undergo piezoelectric vibration, oscillates against a solution 309 in the vial of the vial 308, causing some of the solution to move through the openings and form small particles on or above the outer surface of the active mesh 310. In some embodiments, active mesh 310 vibrates at from about 80 kHz to about 200 kHz upon electrical stimulation by an electrical current directed to the active mesh 310 by a controller board 307 and/or a mesh controller 303 (when present), although active mesh nebulizers having other vibrational frequencies are also within the scope of the present disclosure. In some embodiments, the active mesh is made of pure titanium, platinum, or palladium, or alloys thereof or the like, or laminated layers of titanium, platinum, or palladium or the like, to produce the piezoelectric effect that results in mesh vibration and particle formation over the outer surface of the mesh in the mouthpiece interior volume. In some embodiments, the active mesh is a stainless steel layer. In some embodiments, the active mesh is a polymer layer with openings therethrough. Examples of polymer include polyimide, and the like. In some embodiments, the active mesh includes nylon, polyethylene, and/or Teflon. In at least some embodiments, active mesh 310 is other than disc-shaped. In at least some embodiments, active mesh 310 is polygonal-shaped, rectangular-shaped, ovoid-shaped, elliptical-shaped, or the like.

According to some embodiments, the distribution of particle sizes in the plume of particles is configured to compensate for particles absorbing moisture during travel through the lung airways. As the particles pick up fluid from moisture in the lung, particle diameter increases. Particles which have a solution with a pH not equal to 7 have the pH adjust toward 7 by absorption of liquid from the lungs. When particles become too large, the likelihood of particles striking a lung surface prior to reaching an alveolar structure is increased.

Vial (or a vial assembly) 308 is located inside nebulizer body 306 and fits against a back side of a mouthpiece baseplate 312. A gasket 311 seals the juncture between the vial 308 and the backside of the mouthpiece baseplate 312 to prevent a solution 309 in the vial 308 from leaking. The vial 308 is sealed prior to connection to gasket 311 and mouthpiece baseplate 312 to prevent contamination, spillage, replacement, or removal of the solution 309 to ensure proper concentrations of pharmacological compound are delivered to a patient or user, and to avoid accidental over dosage of the patient or user by an unknown or unanticipated compound added to the vial before or during nebulizing of the solution 309 in the vial. In some embodiments, vial 308 is configured to hold from 1 to 10 milliliters (mL) of pharmacological compound solution, although other vial sizes, both larger than 10 mL, and smaller than 1 mL, are also within the scope of the present disclosure. In some embodiments, the vial is configured with a volume of about 6 mL and is configured to hold from 3 to 5 mL of pharmacological compound solution for the nebulizer 300. The volume of the vial 308 depends on the dosage, the frequency of doses, the value or volatility of the solution.

A controller board 307 in nebulizer body 306 regulates operation of the nebulizer 300. Controller board 307 includes a processor 316, a data storage 318, and an input/output (TO) controller 320. IO controller 320 is connected to a port 330 extending through an outer wall of the nebulizer body 306. In some embodiments, port 330 does not extend through the outer wall of the nebulizer body 306 and communicates data and/or power wirelessly with elements external to the nebulizer body 306. In some embodiments, the processor 316 drives a mesh controller 303 that triggers the operation of the active mesh 310. In some embodiments, the processor operates the active mesh 310 independently without a mesh controller 303. In some embodiments, controller board 307 includes a wireless communication chip 322, an authentication controller 324, and/or a power regulator 326. In some embodiments, port 330 is a port configured to conduct power into a power supply 328 by use of controller board 307. In some embodiments, the power supply is a battery. In some embodiments, the power supply provides a voltage to the controller board and the active mesh ranging from 1.5 volts to 9 volts. In some embodiments, the power supply is a lithium titanate battery having a supply voltage of about 4.8 volts. In some embodiments, port 330 is configured to carry data between controller board 307 and an external computing device or a computer network adapter connected to the port 330. In some embodiments, port 330 is configured to conduct both power and data in order to promote configuration and/or operation of the nebulizer 300. In some embodiments, port 330 is a universal serial bus port or other power/data transfer port for computing devices known to practitioners of the art.

In some embodiments, a connected device, or an external computing device, sends instructions to the processor 316 in order to regulate operation of the active mesh, which are configured to determine performance parameters of the nebulizer. Performance parameters of the nebulizer include a start time of plume production, an end time of plume production, a duration of plume production, and a calculated volume of delivered solution, and a calculated amount of delivered pharmacological compound (e.g., a dose). In some embodiments, software instructions stored on the connected device, or external computing device, are configured to cause the active mesh nebulizer to transmit information about the nebulizer performance to the connected device or external computing device. Information about the nebulizer performance includes at least historical information about plume generation, pharmaceutical compounds, active mesh nebulizer performance characteristics, and the like. In some embodiments, the connected device or external computing device shares some or all information received from the active mesh nebulizer with the patient or user, or a third party such as a health care provider, a health care company, and/or a family member of the patient or user. In some embodiments, the external computing device is a tablet computer, a smartphone, a smart watch, a laptop computer, a desktop computer, or the like. In some embodiments, a communicative connection between the active mesh nebulizer and the external computing device is a wired connection over, e.g., a universal serial bus (USB) cable or another direct wired connection. In some embodiments, the communicative connection between the active mesh nebulizer and the external computing device is a wireless connection, as described below.

In some embodiments, authentication controller 324 is configured to record a biometric feature of a patient or user such as a fingerprint, iris image, retinal image, facial pattern, or other biometric identifying feature, or a password, passcode, electronic identifying code, or other security protocol or feature to restrict usage of the nebulizer 300 to approved or authenticated users, including users to whom the nebulizer 300 has been prescribed by a health care professional or other device supplier. In some embodiments, nebulizer 300 includes a fingerprint reader (not shown) to capture a fingerprint image for authentication. In some embodiments, a connected electronic device (such as a cell phone, tablet, smart watch, or other authenticated device) contains a biometric feature identifier such as a fingerprint reader, camera, or electronic password, passcode, electronic identifying code, or other security protocol interface to receive, from a user, the identifying authentication code and share, with the nebulizer 300, (or, the authentication controller 324 therein), the identifying authentication code or biometric feature information. In some embodiments, nebulizer 300 includes a biometric feature identifier such as a camera, or electronic password, passcode, electronic identifying code, or other security protocol interface to receive, from a user, the identifying authentication code and share, with the authentication controller 324 therein, the identifying authentication code or biometric feature information. In some embodiments, authentication controller 324 is configured to prevent activation of the active mesh by the processor until an authentication code or authorized biometric feature information has been received and verified by the authentication controller 324.

In some embodiments, the authentication controller performs authentication functions regarding a connected device, or an external computing device, which pairs, using an authentication protocol, to the nebulizer to reduce a likelihood of unauthorized use of the nebulizer when the connected device or external computing device is not present. In some embodiments, the connected device receives information from the nebulizer related to an identifier on the vial and compares information associated with the identifier on the vial to information related to the nebulizer and/or the external computing device, to confirm that the vial contains an anticipated and/or authorized pharmacological compound, that the vial contains an anticipated and/or authorized concentration of the pharmacological compound, that the vial is one of a number of anticipated and/or authorized number of vials linked, by the identifier, and/or information stored on at least the nebulizer and/or connected device (or external computing device) to the nebulizer to deliver the anticipated and/or authorized pharmacological compound to the patient or user. In some embodiments, a health care provider (such as a pharmacist, a physician, a physician's assistant, a nurse, or other authorized health care provider) inputs into the device the information to be accessed by the authentication controller. In some embodiments, the information is put on the connected device or external computing device.

In some embodiments, the nebulizer does not contain an on/off switch. In some embodiments, the nebulizer reads the identifier, verifies that the identifier is one of the approved identifiers associated with the nebulizer and any external computing device. In some embodiments, the nebulizer, after verifying that the identifier is on the list of approved identifiers, verifies that the nebulizer body is and remains closed. In some embodiments, when the identifier is verified to be approved, and when the nebulizer body is verified to be and remain closed, the processor 316, in conjunction with authentication controller 324, enables activation of the active mesh 310 upon a dosage request by a patient or user of the nebulizer.

Figure 6:
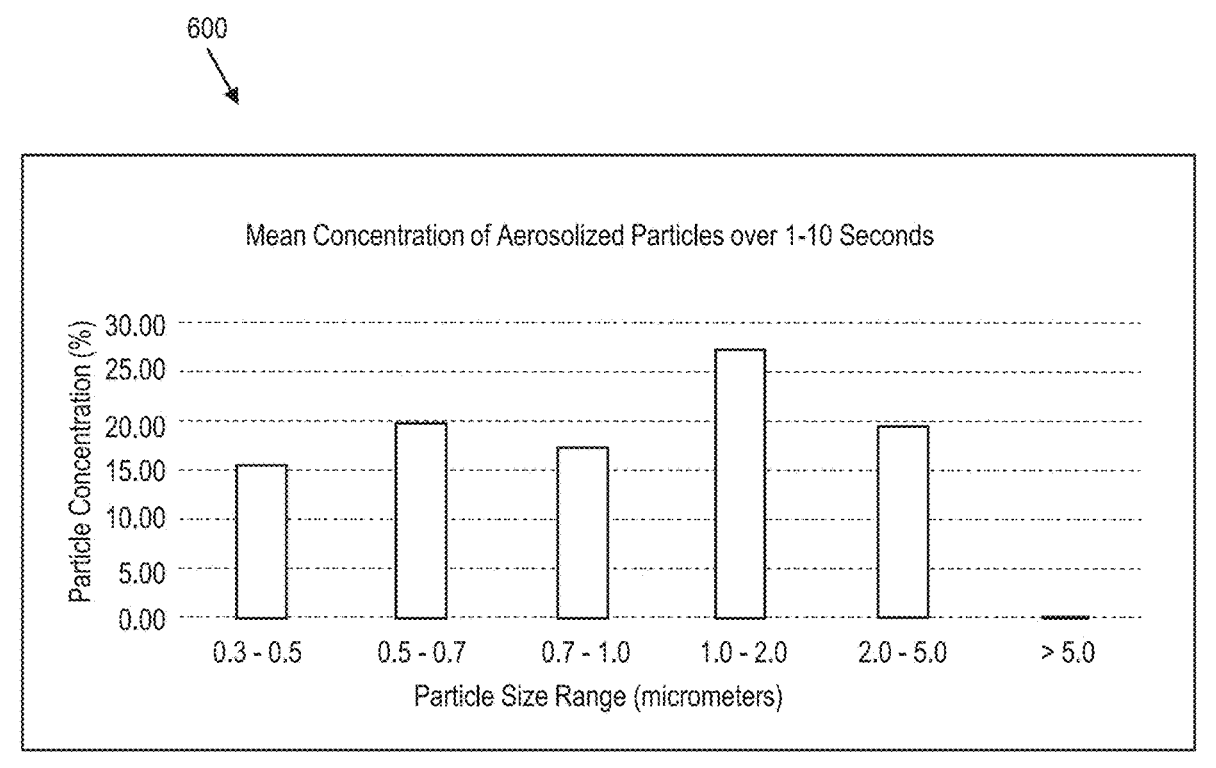

In some embodiments, vial 308 is configured with a vial identifier 313 (an "identifier"). In some embodiments, the identifier 313 is a barcode on a wall of the vial 308. In some embodiments, the barcode is printed directly on the vial. In some embodiments, the barcode is printed on a label that adheres to the wall of the vial. A printed label is used in some embodiments when elevated levels of reflectance are indicated to promote optical reading of a barcode. In some embodiments, the identifier 313 is a chip that performs an RFID (radio frequency identification) function, where the identifier provides information stored thereon, when requested, to the nebulizer 300. In some embodiments, the identifier 313 is an RFID chip located at a base of the vial (see, e.g., FIG. 6B, element 602). In some embodiments, the identifier 313 is a near field communications (NFC) chip. In some embodiments, nebulizer 300 includes a reader 314 configured to capture information from the identifier 313 on a vial 308. In some embodiments, the reader 314 is an optical reader that scans a barcode-type identifier on a vial. In some embodiments, the reader is an RFID-type reader that requests and receives information stored on the identifier in the nebulizer body. In some embodiments, the reader includes at least one set of probes or pins which make electrical contact with the identifier 313. The reader reads information from the chip, and, in some embodiments, writes information to the chip. In some embodiments, the reader performs a write function to the identifier to indicate that the vial has been used and the full dose of medication has been delivered. In some embodiments, writing the information to the identifier 313 results in the vial being locked out from subsequent use in the nebulizer.

Controller board 307 includes the processor 316 and at least a non-transitory, computer-readable storage medium such as data storage 318 encoded with, i.e., storing, computer program code, i.e., a set of executable instructions. Data storage 318 is also encoded with instructions for executing a method of operating the nebulizer (FIG. 2). The processor 316 is electrically coupled to the data storage 318 via a bus 315 or other communication mechanism. The processor 316 is also electrically coupled to an IO controller 320 by the bus 315. Port 330 is also electrically connected to the processor 316 via the bus 315. Port 330 is configured to conduct communication and charging functions for the active mesh nebulizer 300. In some embodiments, port 330 conducts information via wireless communication protocols. In some embodiments, port 330 conducts data to an external computing device via a direct wired connection to an external computing device. In some embodiments, active mesh nebulizer 300 conducts data to an external computing device via a wireless connection to an external computing device. In some embodiments, port 330 conducts data to an external computing device over a wired network connection, and processor 316 and data storage 318 are capable of connecting to external elements or external computing devices via the network. In some embodiments, the processor 316 and the data storage 318 are configured to both send and receive data between the active mesh nebulizer 300 and an external computing device. The processor 316 is configured to execute the computer program code encoded in the data storage 318 in order to cause the nebulizer to be usable for performing a portion or all of the operations as described in the method.

In some embodiments, the processor 316 is a central processing unit (CPU), a multi-processor, a distributed processing system, an application specific integrated circuit (ASIC), and/or a suitable processing unit.

In some embodiments, the data storage 318 is an electronic, magnetic, optical, electromagnetic, infrared, and/or a semiconductor system (or apparatus or device). For example, the data storage 318 includes a semiconductor or solid-state memory, a magnetic tape, a removable computer diskette, a random access memory (RAM), a read-only memory (ROM), a rigid magnetic disk, and/or an optical disk. In some embodiments using optical disks, the data storage 318 includes a compact disk-read only memory (CD-ROM), a compact disk-read/write (CD-R/W), and/or a digital video disc (DVD).

In some embodiments, the data storage 318 stores the computer program code configured to cause controller board 307 to perform the method. In some embodiments, the data storage 318 also stores information needed for performing the method as well as information generated during performing the method, such as data and/or a set of executable instructions to perform the operation of the method.

In some embodiments, the data storage 318 stores instructions for interfacing with machines. The instructions enable processor 316 to generate instructions readable by the machines to effectively implement the method during a process.

Nebulizer 300 includes IO controller 320. IO controller 320 is able to be coupled to external circuitry. In some embodiments, IO controller 320 includes a touchscreen, keyboard, keypad, mouse, trackball, trackpad, and/or cursor direction keys for communicating information and commands to processor 316.

Nebulizer 300 also includes a network interface, e.g., in the form of port 330, coupled to the processor 316. The network interface allows nebulizer 300 to communicate with a network, to which one or more other computer systems are connected. The network interface includes wireless network interfaces such as BLUETOOTH, WIFI, WIMAX, GPRS, or WCDMA; or wired network interface such as ETHERNET, USB, or IEEE-1394. In some embodiments, the method is implemented in two or more systems, and information are exchanged between different systems via the network.

FIG. 4 is a flow diagram of a method 400 of operating a nebulizer, e.g., nebulizer 300 (FIG. 3), in accordance with some embodiments. According to some embodiments of the present disclosure, the operations listed below are performed in the order described. In some embodiments, additional operations are performed in conjunction with the method to promote safe operation of a nebulizer to deliver doses of pharmacological compounds to a patient or user. In some embodiments, the operations listed below are performed in a different order than provided below, while still falling within the scope of the present disclosure to deliver a pharmacological compound to a patient or user.

Method 400 includes an operation 405, where a patient or user provides a request to a nebulizer and the nebulizer receives the request for a dose of a pharmacological compound. In some embodiments, the patient or user provides the request by pressing a button on the nebulizer body. In some embodiments, the patient or user provides the request by activating the nebulizer using a smartphone, computer tablet, or other electronic device that is communicatively paired with the nebulizer via the IO controller 320 on controller board 307. In some embodiments, the request is provided and received wirelessly using a wireless electronic communication such as WIFI™, Bluetooth™, or another wireless communication protocol. In some embodiments, the request is provided over a direct or wired connection to the IO controller 320 on controller board 307 through a communication port such as port 330.

Method 400 includes an operation 410, wherein the processor 316 determines whether a dosage limit has been reached for the patient or user at the time the patient or user makes the request to the nebulizer to provide a dose of the pharmacological compound. A dosage limit is a limitation on the total deliverable amount of pharmacological compound that is to be delivered to a patient or user during a dosage limitation period. Some dosage limits are related to short term (e.g., less than 12 hours) delivery periods for a pharmacological product. Some dosage limits are related to long term (e.g., greater than 12 hours, up to several days) delivery periods of a pharmacological product. In some embodiments, when determining whether a dosage limit has been reached, the processor 316 accesses data storage 318 to evaluate previous times of delivery of the pharmacological compound to the patient or user. In some embodiments, when determining whether a dosage limit has been reached, the processor 316 accesses data storage 318 to evaluate previous amounts of delivered pharmacological compound to the patient or user.

In some embodiments, the dosage limit is stored in the data storage 318. In some embodiments, the dosage limit is stored on vial 308 as part of identifier 313 and read by reader 314 for storage in data storage 318. In some embodiments, the dosage limit is received from a device external to nebulizer 300 via port 330 and IO controller 320.

When, based on at least one of the previous times of delivery of the pharmacological compound and the previous amounts of delivered pharmacological compound, the dosage limit of the pharmacological compound has been reached, method 400 proceeds to operation 412, wherein the active mesh is prevented from activating to deliver pharmacological compound until a delay period (e.g., a dosage delay period or dosage delay time) has elapsed. In some embodiments, the delay period is based on a calculated time in which a patient or user is expected to metabolize previously delivered pharmacological compound, including an amount of previously delivered pharmacological compound provided to the patient or user. In some embodiments, the delay period is based on a pre-determined time period associated with providing doses of the pharmacological compound. In some embodiments, the delay period is programmed into the nebulizer based on instructions from a health care provider or health care professional. In some embodiments, the delay period is based on an instruction provided to the nebulizer by the patient or user of the nebulizer. In some embodiments, the delay period is programmed into the nebulizer based on the type of pharmacological compound in the vial loaded into the nebulizer for the patient or user. In some embodiments, the delay period is a combination of one or more of the type of pharmacological compound, an instruction provided by a health care provider or health care professional, and a previously-delivered amount of the pharmacological compound. In some embodiments, operation 412 comprises a period in which the active mesh is not activated as opposed to preventing activation of the active mesh. After operation 412, the method proceeds to operation 405.

When, based on at least one of the previous times of delivery of the pharmacological compound and the previous amounts of delivered pharmacological compound, the dosage limit of the pharmacological compound has not been reached, method 400 proceeds to operation 415. Because the dosage limit has not been met, there is no triggering of a delay period before additional pharmacological compound delivery, and requests for dosing with the pharmacological compound are allowable by the nebulizer.

In operation 415, in preparation to delivering the pharmacological compound, the processor 316 determines an amount of compound to be provided via the active mesh in response to receiving the request received in operation 405. A determined amount of pharmacological compound to be provided in the requested dose is based on one or more of a time of the most recent dose of pharmacological compound, a quantity of the pharmacological compound provided in a most recent dose of the pharmacological compound, and the dosage limit of the pharmacological compound for the patient or user. In some embodiments, the determined amount of pharmacological compound is a full requested dose of compound because the size of a full requested dose (an initial dose size, or a standard dose size) does not exceed the dosage limit of the pharmacological compound. In some embodiments, the determined amount of pharmacological compound is a partial dose (or, a modified dose size), because a full dose of the pharmacological compound exceeds the dosage limit of the pharmacological compound. A dosage limit is based on a quantity of pharmacological compound delivered to a patient or user within a dosing time period. In some embodiments, the dosing time period is determined by a health care provider or professional. In some embodiments, the dosing time period is determined by the patient or user of the nebulizer. In some embodiments, the dosing time period is based on an average metabolism rate of the pharmacological compound by a patient or user.

Although previous discussion related to dose size calculation based on reductions in dose size, reductions in vibration time period of the active mesh, and smaller modified dose sizes in relation to delivering pharmacological compounds that approach a dosage limit of the pharmacological compound, aspects of the present disclosure also relate to determinations of increased vibration time of the active mesh, increased dose size (or repeated dosing in a short period of time), or larger modified dose sizes. Increases in dosing frequency, increased modified dose sizes, and increased vibration time period of the active mesh are most appropriate "early" in a dosage cycle, when a patient or user is not near to a dosage limit or dosage threshold of the pharmacological compound. In a non-limiting example, pain medication is delivered on demand to a patient or user upon a dosage request as often as a patient requests until the dosage threshold has been achieved, in order to address a patient's perceived pain levels. Should a patient continue to request pain medication at increased rates, the nebulizer is configured to provide information to medical providers about a number of times pain medication was requested, frequency of the requests, information about the medication being delivered, and medical providers are enabled to modify medications, modify limits of the medication delivery schedule or dosage limits, or initiate patient counseling or rehabilitative treatments to address addictive patterns of behavior before a patient becomes physically or mentally dependent on or addicted to the pain medication.

Method 400 includes an operation 420, wherein, based on a predetermined amount of pharmacological compound to be provided via the active mesh to the patient or user, the nebulizer determines at least one vibration time period (e.g., a calculated vibration time) of the nebulizer active mesh in order to deliver the pharmacological compound to the patient or user. The at least one vibration time period of the active mesh is determined based on one or more of the characteristics of the active mesh, the concentration of solute(s) in the solution of pharmacological compound in a vial in a nebulizer, a quantity of pharmacological compound to be provided, and whether or not the full requested dose is to be provided based on the dosage limit of the pharmacological compound.

Method 400 includes an operation 425, wherein the active mesh is activated in order to produce a plume of particles or droplets of a solution of a pharmaceutical product to be inhaled by a patient or user. In some embodiments, the nebulizer signals to the patient or user to begin inhaling through the mouthpiece 302 before the active mesh is activated to produce the plume of particles or droplets. One aspect of the present disclosure related to controlled and/or accurate dosage of the pharmacological product being provided to the patient or user is to generate an entirety of a plume of particles or droplets during a single inhalation event by the patient or user. The timing of the active mesh is controlled in order to produce a well-defined quantity of particles or droplets in the plume. In some embodiments, the timing of the active mesh is controlled to within +/−0.2 seconds when starting and stopping the mesh vibration to produce a plume of particles or droplets. In other embodiments, the timing of the active mesh is controlled to within +/−0.5 seconds or greater. In some embodiments, the period of time for generating a plume of particles is a plume generation interval. The total vibrational time of the active mesh is divided into a set of plume generation intervals to divide delivery of the mediation/pharmaceutical product into portions that can be inhaled by a user without interruption, where each plume generation interval corresponds to a period of time for generating one plume portion.

In some embodiments, after a vial 308 with solution is removed from the nebulizer 300, the active mesh is cleaned by activating the mesh with a vial of cleaning solution therein. In some instances, the cleaning solution is water. In some embodiments, the cleaning solution contains other antibacterial compounds for killing bacteria. Cleaning an active mesh eliminates biological contaminants that cause illness. For example, bacterial growth on an uncleaned active mesh is included in a plume of particles when no cleaning occurs, which contributes to elevated rates of respiratory illness in some patients or users of nebulizers. In some embodiments, the active mesh is cleaned on at least a daily basis. In some embodiments, the active mesh is cleaned on a weekly basis. In some embodiments, the active mesh is cleaned with soap and water. After cleaning, the active mesh is allowed to air-dry. During cleaning, it is not recommended to bring solid objects into contact with the active mesh because the grid is prone to damage. For example, fingers, cotton swabs, cleaning cloths, and so forth, are amount the solid objects which are not recommended to come in contact with the active mesh because of the high likelihood of grid damage occurring.

According to some embodiments, the active mesh is vibrated for a cleaning period of at least 1 second, and up to 10 seconds, in order to remove contaminant materials from the active mesh surface, although cleaning periods longer than 10 seconds are also contemplated within the scope of the present disclosure. In some embodiments, the active mesh is vibrated when the solution in a vial 308 is in direct contact with one surface of the active mesh, in order to produce a cleaning plume, where the solution in the vial 308 flushes through the openings in the active mesh, to produce particles that are not for inhalation by a patient or user.

Figure 5:
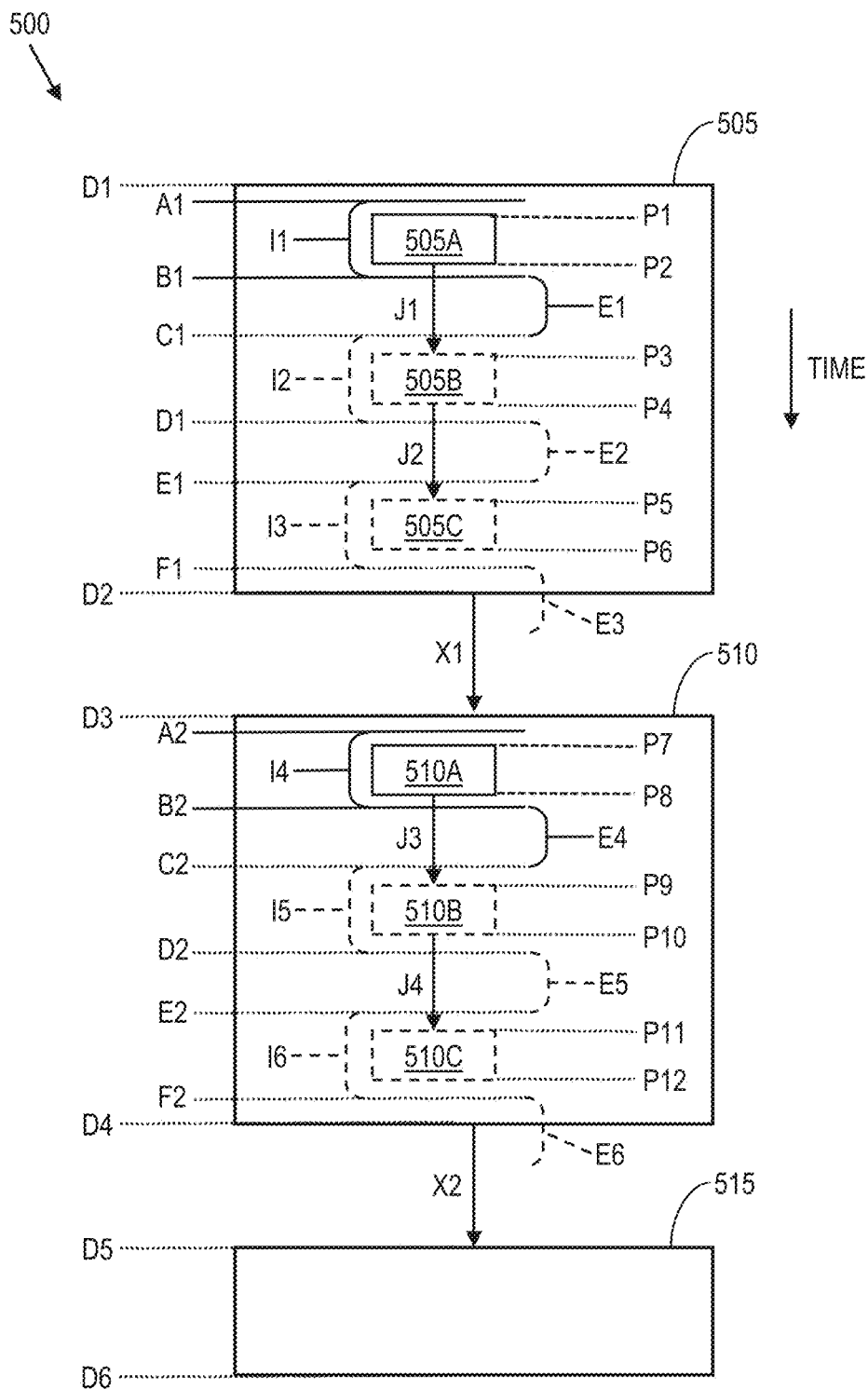

Method 400 includes an operation 430, wherein the active mesh is deactivated after providing some or all of a determined amount of the pharmacological compound. In some embodiments, the requested amount of the pharmacological compound is provided in a single activation period of the active mesh. In some embodiments, the requested amount of the pharmacological compound is provided over the course of several activation periods of the active mesh. Further discussion of the timing and duration of activation periods of the active mesh during delivery of a determined amount of pharmacological compound follows in the discussion of FIG. 3. In some embodiments, when the total vibration time period of an active mesh to produce a plume of particles or droplets containing the determined amount of pharmacological compound exceeds a breath duration value (or an inhalation duration time), the total vibration time of the active mesh (see Plume Generation Interval, PGI, below) is divided into smaller time periods (smaller vibration time periods, or modified vibration times) that are smaller than a breath duration value (or an average breath duration of a patient or user) to avoid producing a plume of droplets or particles when the patient is not inhaling the plume into the lungs.

In an operation 435, the processor 316 determines whether the determined amount of pharmacological compound has been delivered. Determination of whether the determined amount of pharmacological compound has been delivered is made by using at least a computed vibrational time period of the active mesh, an actual or measured vibrational time of the mesh, and a calibration value of the active mesh for producing a plume of particles of a solution in a vial in the nebulizer. In some embodiments, the determination further includes a calibration value for the total solute concentration of the solution in the vial, which has an impact on at least particle (or droplet) size in the plume of particles, and the mass flow of solution through the active mesh openings to make the plume of particles. When the determined amount of pharmacological compound has been delivered to the patient or user, the method continues to operation 410, wherein a determination is made about whether the dosage limit has been reached. When the determined amount of pharmacological compound has not been delivered to the patient or user, the method proceeds to operation 425 for at least one subsequent or second activation period of the active mesh to deliver a remainder of the determined amount of pharmacological compound. In some embodiments, the total vibration time of the active mesh is divided into uniform intervals to deliver the determined amount of pharmacological compound (and the at least one vibration time period of the active mesh is uniform). In some embodiments, the total vibration time period of the active mesh is divided into non-uniform intervals to deliver the determined amount of pharmacological compound (and not all of the at least one vibration time periods of the active mesh are uniform). Uniform intervals are advantageous to help patients keep track of dosing progress and account for any missed plume inhalation time periods when determining total amounts of delivered pharmacological compound, or when reporting dosing received from the nebulizer to a health care provider or other third party. In some embodiments, non-uniform intervals are advantageous to deliver a maximum dosing of a pharmacological compound to a patient in the shortest amount of time or number of breaths.

FIG. 5 is a diagram of a nebulizer dosing program 500, in accordance with some embodiments. Nebulizer dosing program 500 includes a first dosing session 505 and a second dosing session 510. First dosing session 505 begins at a time D1 and ends at a time D2. A second dosing session 510 begins at a time D3 and ends at a time D4. A third dosing session 515 begins at a time D5 and ends at a time D6. Each dosing session includes at least one plume generation period, e.g., plume generation period 505A (or mesh activation period, see operations 420, 425, and 430 of method 400 in FIG. 4, above).

Each dosing session also includes at least one inhalation period, such as inhalation period I1 in first dosing session 505, and inhalation period I4 in second dosing session 510. In some embodiments, first dosing session 505 includes at least one additional inhalation period, such as inhalation periods I2 and I3, and second dosing session 510 includes at least one additional inhalation period, such as inhalation periods I5 and I6. Exhalation periods E1-E6 follow inhalation periods. For example, exhalation period E1 follows inhalation period I1 and precedes inhalation period I2. Some exhalation periods follow an inhalation period and a plume generation period, but are not considered part of a dosing session (see, e.g., exhalation period E3 after inhalation period I3, and exhalation period E6 after inhalation period I6).

Each inhalation period has an inhalation duration, and each exhalation period has an exhalation duration. In first dosing session 505, inhalation duration of inhalation period I1 extends from time A1 to time B1 [e.g., Inhalation Duration (ID)=Inhalation End Time (IET)−Inhalation Start Time (IST), see Table 1, below]. In first dosing session 505, exhalation duration of exhalation period E1 extends from time B1 to time C1 [e.g., Exhalation Duration (ED)=Exhalation End Time (EET)−Exhalation Start Time (EST), see Table 2, below]. First dosing session 505 includes plume generation period 505A. Plume generation period 505A extends from time P1 to P2 [e.g., plume duration (PD) =Plume End Time (PET)−Plume Start Time (PST), see Table 3, below]. In some embodiments, first dosing session 505 also includes at least one additional plume generation period, such as plume generation periods 505B and 505C.

When, in a dosing session, there are two or more inhalation periods and two or more plume generation periods, a pause (J) between adjacent plume generations periods extends from the end of one plume generation period and the start of a next plume generation period within the dosing session. For example, in first dosing session 505, pause J1 is between plume generation period 505A and plume generation period 505B, having a pause duration matching the time difference between time P3 and time P2 (e.g., P3-P2, see first dosing session 505, FIG. 5), and pause J2 is between plume generation period 505B and plume generation period 505C, having a pause duration matching the time difference between time P5 and time P4 (e.g., P5-P4).

In each dosing session, plume generation occurs for less time than the inhalation duration of the inhalation period of the patient or user. In some embodiments, plume generation both commences after the start of an inhalation period and ends before the end of the inhalation period. In some embodiments, plume generation begins before or at the same time as an inhalation period and ends before the inhalation period ends. In embodiments where plume generation begins before, or at the same time as, an inhalation period, the duration of any plume generation before an inhalation period is sufficiently short that the plume of generated particles is retained within the interior volume of the mouthpiece without flowing out of openings in the mouthpiece configured to allow air to pass between the interior volume and the exterior volume from the mouthpiece. In a preferred embodiment, the duration of a plume generation period is smaller than an inhalation period duration in order to increase the likelihood that the contents of the generated plume of particles or droplets is brought into the lungs without wasting portions of the plume by not being inhaled into the lungs.

In some embodiments of the nebulizer, the nebulizer indicates to a patient or user that an inhalation period should begin with commencement of a first signal or a first alarm (one or more of a vibration, a flashing or constant light, or, in the case of a user with visual impairment, a sound played by the nebulizer or the connected electronic device that triggers operation of the active mesh to produce a plume of particles or droplets). Generation and/or cessation of signal or alarms is indicated in operations 425 and 430 of method 400, described above. In some embodiments, the p user is informed that an inhalation period may end (because the plume production has stopped) with a second signal or second alarm, different from the first signal or first alarm. In some embodiments, the patient or user is informed that an inhalation period has ended with a cessation of the first signal or first alarm, which has remained continuous throughout the inhalation period. In some embodiments, the first signal or the second signal is a combination of one or more of a vibration, a flashing or constant light, or a sound played by the nebulizer or connected electronic device that triggers operation of the active mesh. In some embodiments, the first signal is one or more of a vibration, a light signal, or a sound played by the nebulizer or the connected electronic device, and the second signal is a different of one or more of a vibration, a light signal, or a sound played by the nebulizer or the connected electronic device. In some embodiments, signaling to indicate the commencement and ending of inhalation is repeated for each inhalation until a determined amount of pharmacological compound has been delivered by the nebulizer, up to a dosage limit of the pharmacological compound, or until a time threshold is reached at which point the nebulizer operation is halted.

In some embodiments, a connected device sends signals to start and/or stop vibration of the active mesh to produce a plume of particles or droplets. In some embodiments, a connected device records the times and durations of active mesh activation, active mesh deactivation, calculated volumes of delivered pharmacological compound based on the recorded start times, stop times, and plume generation period durations for the nebulizer. In some embodiments, the connected device stores the information for subsequent transmission to a third party, including a health care provider or health-care company, or a family member of the patient or user.

A dosing session ends when the last plume generation period ends. Thus, in some embodiments, a dosing session end time coincides with the plume generation period ending time. Thus, in a non-limiting example, dosing period 505 ends at time D2, and time D2 may, in some embodiments, coincide with time P6. In some embodiments, time F1 also coincides with time P6.

A waiting period X1 extends from time D2 to time D3. A delay period X2 occurs when the patient must wait before receiving another dose and extends from time D4 to time D5 (the start of a dosing session 515, see FIG. 5). Waiting period X1 is initiated by completion of a dosing session 505 and extends to the start of dosing session 510, wherein the nebulizer is able to provide another dose of a pharmacological compound to a patient or user at any time. Delay period X2 is initiated by completion of dosing session 510 and extends to the start of dosing session 515, wherein the operation of the active mesh in a nebulizer is blocked or halted because a patient or user has met a dosage limit of the pharmacological compound being delivered. A person of ordinary skill will recognize that other nebulizer dosing programs are also within the scope of the present disclosure while still meeting the medical treatment plans of a patient or user, or of satisfying a patient or user's at-will requests for nebulized doses of pharmacological compound, while still avoiding scenarios where an excess of compound is delivered to the patient or user within a prescribed time period.

Time periods, events, and durations for dosing session 510 are labeled in a manner similar to dosing session 505, where the time labels A-F have terminal numbers incremented by 1, where pause identifiers (J) have terminal numerals incremented by 2, inhalation identifiers (I) and exhalation identifiers (E) have terminal numerals incremented by 3, and plume generation (P) time labels have terminal numerals incremented by 6, as compared to dosing session 505.

In some embodiments, the inhalation duration is an averaged value programmed into the nebulizer storage to regulate the duration of a plume generation period. In some embodiments, the inhalation duration is a value entered into the nebulizer storage by a health care professional, health care company, the patient or user, or a third party, to accommodate a patient or user's individual lung capacity or breathing pattern. In some embodiments, the plume generation period is equal, or evenly distributed, throughout a dosing session. In some embodiments, the plume generation period is unevenly distributed through a dosing session. A range of the inhalation duration is from about 2 seconds to about 10 seconds, although longer inhalation times are also within the scope of the present disclosure to accommodate patients with larger lung capacity or who are to be accommodated during nebulizer use with longer inhalation times for medical reasons (obstructed airways, which reduces the peak inhalation rate, likelihood of coughing or bronchospasm during inhalation, which would result in exhalation of some or all of the plume of particles or droplets before absorption by the lungs, and so forth). According to theory and belief, the small size of the particles produced by the active mesh, as described above, promotes facile entrainment of the particles deep into the lung structure, without particles impacting the lung tissues and triggering a cough reflex in the patient or user.

In some embodiments, the pause time (e.g., J1, J2, and so forth) is programmed into the nebulizer storage to regulate the overall pause duration between subsequent plume generations in a multi-plume dosing session. In some embodiments, the pause time is programmed by a patient or user, or a third party such as a physician, health care provider, health care company, or other third party to allow tuning of the pause time to accommodate individual comfort or breathing conditions of a patient or user to avoid wasting the plume of particles or droplets by coughing, bronchospasm, missing an opportunity to inhale a plume of particles or droplets, and so forth. For a nebulizer which produces a plume of particles ranging between 0.5 and 5 μm in diameter, the particles do not make contact with the lung tissue within the first three bronchial divisions of the lungs, there is no possibility of coughing by the user because the lower ($4^{th}$ and greater) divisions of the bronchii do not have tissue which triggers coughing. In some embodiments, the nebulizer waits for a signal (button press, and so forth, on the nebulizer or a connected electronic device that regulates nebulizer operation) to the nebulizer from the patient or user before beginning a second plume generation period, or a dosing session, to ensure that the patient or user is prepared to inhale the plume of particles or droplets having the pharmacological compound therein. Thus, in some embodiments, the pause time (e.g., J1, J2, and so forth) is a variable time subject to user influence during operation of the nebulizer.

TABLE 1

| Inhalation Periods | | | |
|---|---|---|---|
| Event = Inhalation | Start = Inhalation Start Time (IST) | End = Inhalation End Time (IET) | Elapsed time = Inhalation Duration (ID) |
| I1 | A1 | B1 | B1-A1 |
| I2 | C1 | D1 | D1-C1 |
| I3 | E1 | F1 | F1-E1 |
| I4 | A2 | B2 | B2-A2 |
| I5 | C2 | D2 | D2-C2 |
| I6 | E2 | F2 | F2-E2 |

TABLE 2

| Exhalation Periods | | | |
|---|---|---|---|
| Event = Exhalation | Start = Exhale Start Time (EST) | End = Exhale End Time (EET) | Elapsed time = Exhale Duration (ED) |
| E1 | B1 | C1 | C1-B1 |
| E2 | D1 | E1 | E1-D1 |
| E3 | F1 | N/A | N/A |
| E4 | B2 | C2 | C2-B2 |
| E5 | D2 | E2 | E2-B2 |
| E6 | F2 | N/A | N/A |

TABLE 3

| Plume Generation Periods | | | |
|---|---|---|---|
| Event = Plume | Start = Plume Start Time (PST) | End = Plume End Time (PET) | Elapsed time = Plume Duration (PD) |
| 305A | P1 | P2 | P2-P1 |
| 305B | P3 | P4 | P4-P3 |
| 305C | P5 | P6 | P6-P5 |
| 310A | P7 | P8 | P8-P7 |

TABLE 3-continued

| Plume Generation Periods | | | |
|---|---|---|---|
| Event = Plume | Start = Plume Start Time (PST) | End = Plume End Time (PET) | Elapsed time = Plume Duration (PD) |
| 310B | P9 | P10 | P10-P9 |
| 310C | P11 | P12 | P12-P11 |

TABLE 4

| Pharmacological Compound Dosing Periods | | | |
|---|---|---|---|
| | Dosing Event Start | DosingEvent End | Dosing Event Duration |
| Event = Dosing Event | | | |
| 305 | D1 | D2 | D2-D1 |
| 310 | D3 | D4 | D4-D3 |
| 315 | D5 | D6 | D6-D5 |
| Event = Wait or Delay | | | |
| W1 | D2 | D2 | D3-D2 |
| Y1 | D4 | D5 | D5-D4 |

FIG. 6 is a chart 600 of particle sizes in a plume of particles produced by an active mesh nebulizer disclosed by the present disclosure. In chart 600, the particles produced in the plume of particles are detected using a laser diode particle counter (ParticleScan PRO® model) mounted on a test chamber with a probe directed toward the chamber inner volume. The particle counter is 12 inches from the particle plume, and the test chamber was purged with HEPA filtered air gas. In chart 600, the fraction of particles larger than 5 micrometers is a small fraction of the total number of particles produced by the active mesh nebulizer disclosed by the present disclosure.

FIG. 7 is a table 700 of the average particle size information for each second of the first 10 seconds of active mesh nebulizer plume production by active mesh nebulizer disclosed herein. The values in columns of table 700 are averaged together and plotted to produce chart 600.

FIGS. 8A and 8B are diagrams of a vial assembly 800, in accordance with an embodiment. A vial assembly may be referred to as a cartridge or capsule. Vial assembly 800 includes a vial cage 801. In accordance with an embodiment, the vial cage 801 is constructed of plastic or another suitable material. In accordance with an embodiment, a cryptographic chip 802 is situated within the vial cage 801. An adhesive layer 806 is placed above the cryptographic chip 802. In accordance with an embodiment, the adhesive layer 806 is a very-high bond strength adhesive such as a permanent adhesive. The adhesive layer 806 securely maintains the cryptographic chip 802 in place within the vial cage 801. A vial 803 is adhered to the adhesive layer 806. In accordance with an embodiment, the vial 803 is a chip-resistant Corning Valor glass vial. The vial 803 contains a liquid (not shown). A stopper 804 closes the vial 803 and prevents leakage and contamination of the liquid within the vial 803. A tear-off seal 807 is fixed over the stopper 804. In accordance with various embodiments, the tear-off seal 807 is formed of crimped metal or an adhesive label. In accordance with an embodiment, the color of the tear-off seal 807 is used to identify the liquid within the vial 803. A label 805 is affixed to the vial 803. In accordance with an embodiment, the label 805 includes information regarding the liquid in the vial 803, including a 2D bar code and human-readable printing, containing information regarding the manufacturer of the medication, the medication, the volume of medication, the medication manufacturing lot number and the medication expiration date.

In accordance with an embodiment, the vial assembly 800 is packaged and sent to an ordering pharmacist. The pharmacist programs the patient's prescription information, such as the patient ID, medication, dosing amount, and dosing frequency, into a nebulizer. If the information contained in the cryptographic chip 802 matches the patient's prescription information, which the pharmacist programmed into the patient's nebulizer, the nebulizer dispenses the proper dose of medication at the proper intervals, until the prescribed number of doses have been dispensed. At which time, that vial assembly 800 is locked and no longer usable by the nebulizer to provide any further doses of medication. Each time the nebulizer dispenses a dose of medication, the date, time, and plume duration is written to the non-volatile memory of the active mesh nebulizer 300. This information is read by an external device and sent to the prescribing doctor and patient's insurance company for proof of proper dosing, enabling continued insurance coverage for that medication. In accordance with an embodiment, the nebulizer does not function without the application. The nebulizer tracks usage and writes the use of a dose back to the vial assembly via RFID and does not allow the vial assembly to be used again once the maximum allowed doses are consumed. This information is relayed back to the application via Bluetooth or other communication method such as WIFI or Ethernet.

Figure 4:
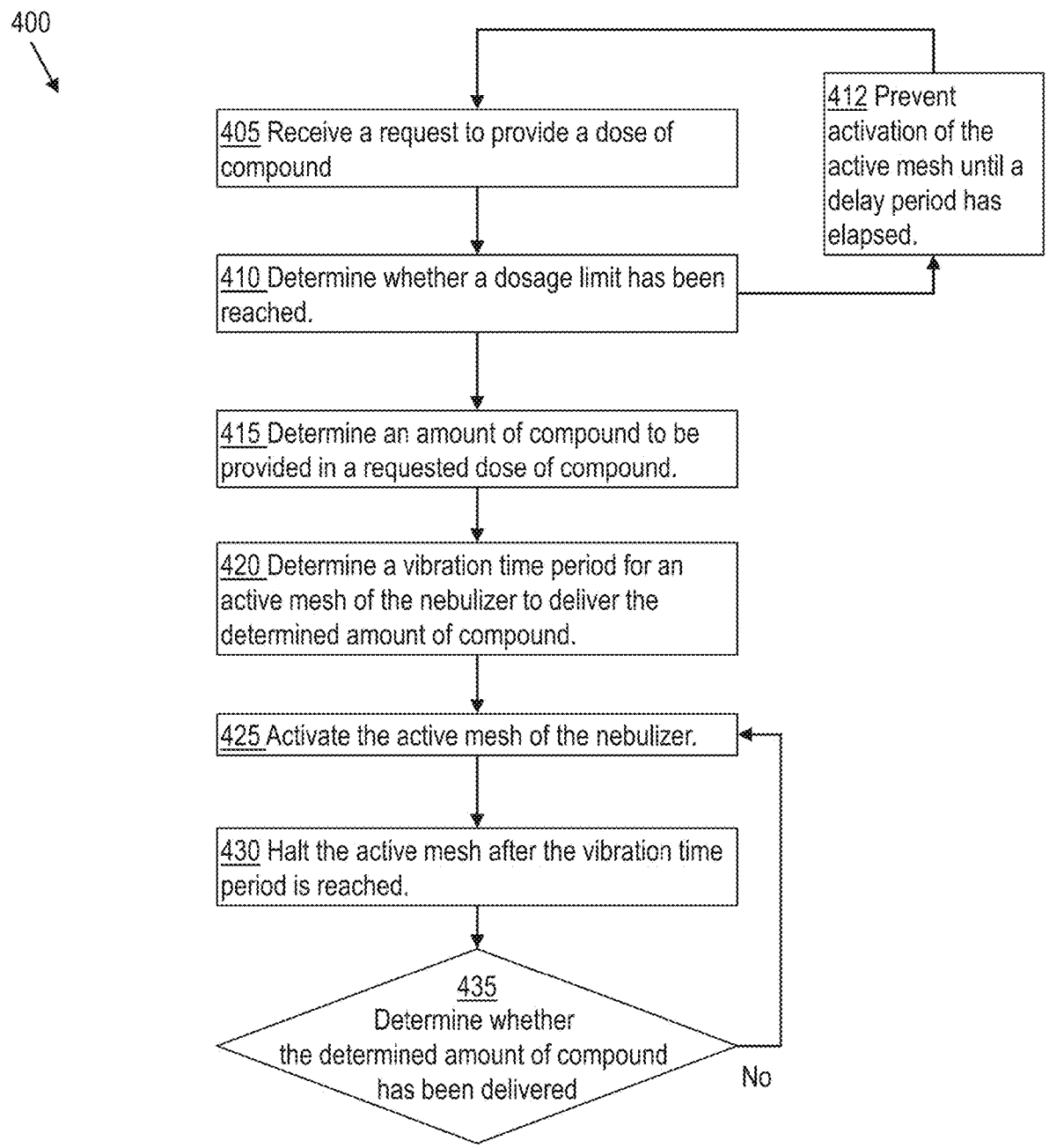
Figure 8A:
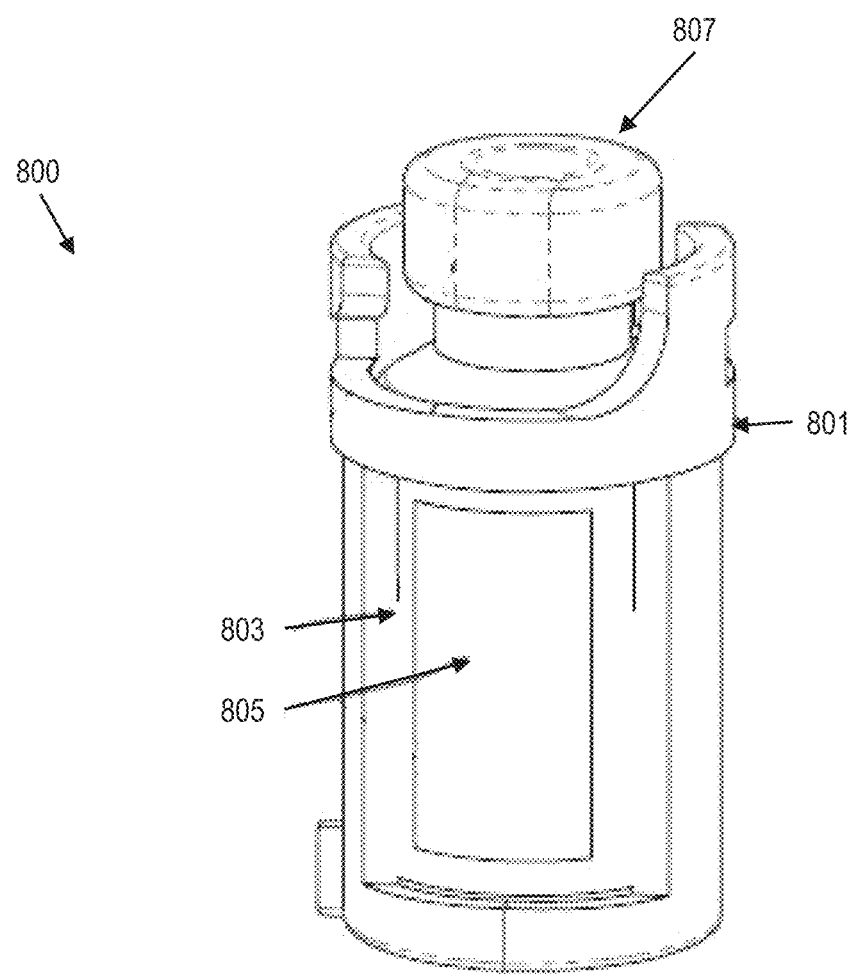
Figure 8B:
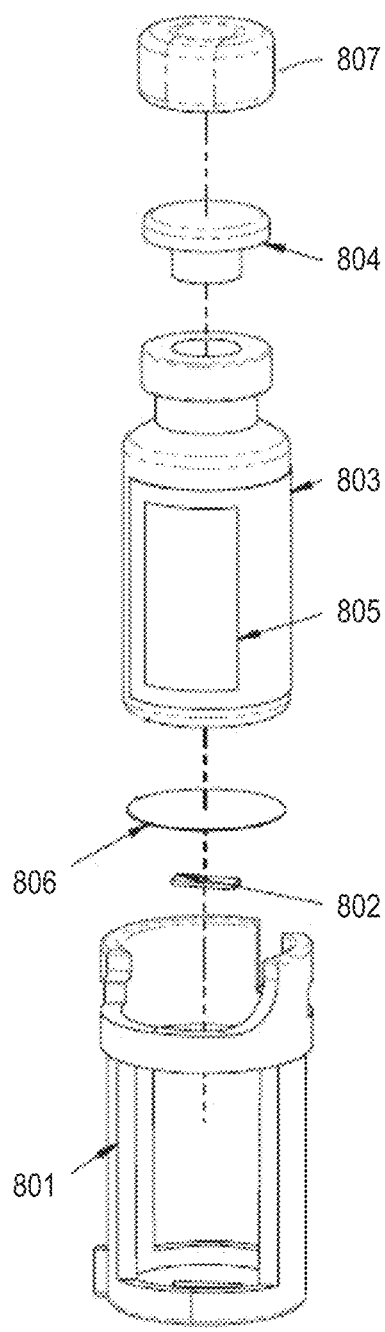
Figure 9A:
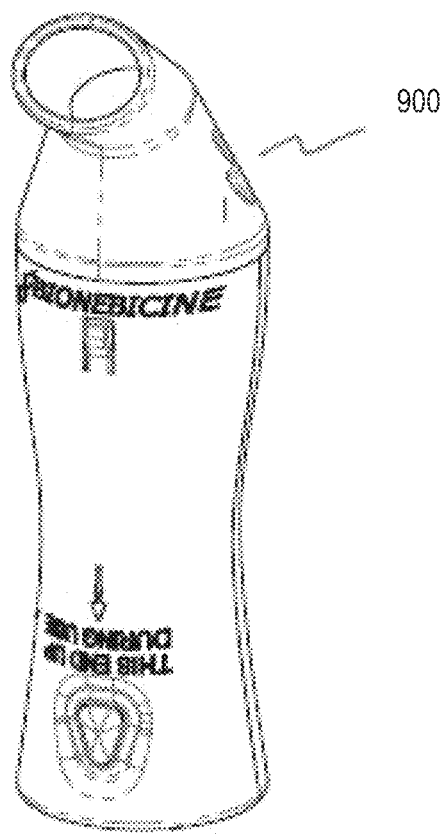
Figure 9B:
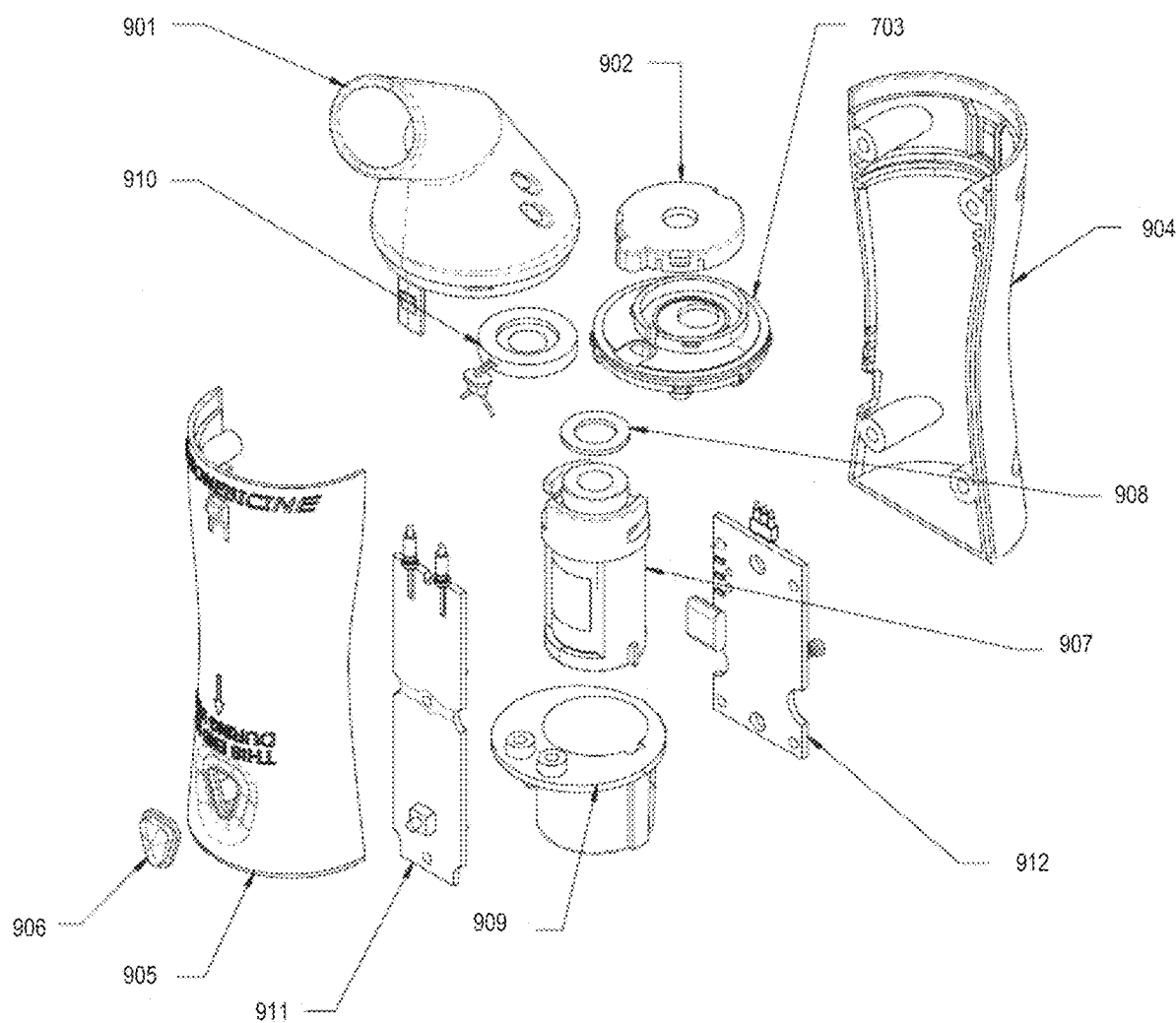

FIGS. 9A and 9B are diagrams of an active mesh nebulizer 900, in accordance with an embodiment. The active mesh nebulizer 900 includes a mouthpiece 901 situated on a handle formed by handle front 905 and handle back 904. A piezo-electric disc 910 is situated between a piezo disc nest 903 and a piezo disc cap 902. An on-off button 906 is situated on the handle front 905. A vial assembly 907, as described in FIG. 8A in connection with vial assembly 800, is placed within a vial receptacle 909 in the active mesh nebulizer 900. A control circuit 911, corresponding to controller board 307 (FIG. 3), controls operation of the piezo disc 910 as set forth in conjunction with method 400 (FIG. 4). A communication circuit 912 communicates with the cryptographic chip, such as cryptographic chip 802, within the vial assembly 907. Control circuit 911 is electrically connected to communication circuit 912 in order to perform data storage and communication functions for the active mesh nebulizer 300.

When ready to receive a dose of medicine from the active mesh nebulizer 900, the patient turns the active mesh nebulizer 900 upside down and pushes the on/off button 906 to begin operation of the active mesh nebulizer 900. When a plume of medicine appears, the patient places the end of the mouthpiece 901 into their mouth and inhales a medication plume. The patient then pushes the on/off button 906 to stop the operation of the active mesh nebulizer 900. When ready to take a next inhalation of medication, the patient repeats the process. After each inhalation, the duration of inhalation, the date, time and vial serial number are written to non-volatile memory in the control circuit 911 in the Nebulizer handle.

Figure 10:
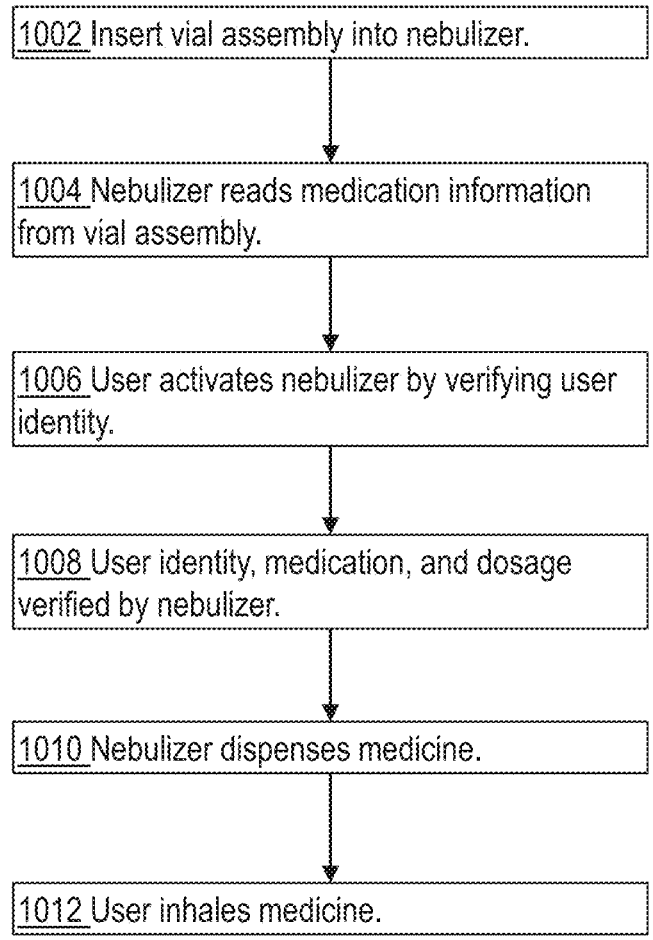

FIG. 10 is a flow diagram of a method 1000 of operating an active mesh nebulizer, in accordance with some embodiments. The method 1000 begins with step 1002 when a user inserts a vial assembly cartridge into the nebulizer. In step 1004, the nebulizer reads medication information from the vial assembly using a bar code reader, RFID, wired pin connector, or the like. In step 1006, the user activates the nebulizer using an app on a smartphone or other device that verifies the user's identity, with a fingerprint reader, a PIN or another suitable method of authentication. In step 1008, using the medication information and the user identity, the nebulizer verifies that the medication is authorized. In accordance with some embodiments, the nebulizer includes a conductivity sensor or pH sensor where the sensor extends into the vial volume on the liquid-side of the nebulizer mesh/grid. By measuring the conductivity of a fluid, the measured value is compared to a "calibrated" value of the fluid as prepared at the packaging plant. When there is a match, the nebulizer operates. When there is a mismatch, the nebulizer does not operate. This prevents the nebulizer from dispensing medicine when the original fluid has been replaced after the vial has been identified to the nebulizer, and before the active mesh is activated. In step 1010, if the medication is authorized, the nebulizer dispenses an appropriate dose of medicine. The user inhales the medication in step 1012.

In accordance with some embodiments, communication between the nebulizer and smartphone app is used to authenticate the user and the medication as well as to control operation of the nebulizer. Security between the nebulizer and the smartphone app is performed using a secure protocol. Communication between the device and the phone is encrypted using proven protocols of encryption (minimum AES-CMAC—AES-128 via RFC 4493, which is FIPS-compliant, or ECDHE aka Elliptic Curve Diffie-Hellman aka P-256, which is also FIPS-compliant).

In accordance with some embodiments, security between the nebulizer and the vial assembly uses a cryptographic chip on the vial assembly to verify that the vial assembly is valid and then authorize its use in the nebulizer. This cryptographic chip provides the ability to store the number of uses or activations, which are limited via this same chip. The cryptographic chip, in accordance with an embodiment, is the SHA204A and a supplemental PIC16. The encryption protocol uses a 256-SHA hashing algorithm on this chip in hardware. This is pre-programmed with hashes in the nebulizer to increase the speed of decryption as an option.

A hash with the secret key are compared between the nebulizer and the vial assembly and a match allows the usage of that vial assembly. A write once area on the cryptographic chip provides the ability to record the delivery of the full dose of medication, with the date and time of delivery to a user. Information related to the total number of uses of the nebulizer is stored in the non-volatile memory of the active mesh nebulizer.

The smartphone app prevents use of the nebulizer by an unauthorized user of the phone. The application opens and allows simple usage of the application, but upon activation of the 'activate nebulizer' command, the phone either requires a fingerprint or PIN or like identification of the user. Otherwise, the command to activate the nebulizer does not display.

In accordance with an embodiment, the nebulizer does not function without the application. The nebulizer tracks usage and writes the use of a dose back to the non-volatile memory in the nebulizer. This information is relayed back to the application via Bluetooth between the active mesh nebulizer and an authorized external computing device communicating with the active mesh nebulizer.

A single-insertion vial assembly allows the vial assembly to be inserted only one time, but when removed the vial assembly would not be able to be reinserted. In some embodiments, a single-insertion vial assembly is used to deliver a single large dose of a medication. In some embodiments, a single-insertion vial assembly is used to deliver multiple small doses of a medication or pharmacological compound before the vial assembly is removed. In some embodiments, the reinsertion of a used vial assembly is possible, but the nebulizer is programmed to not operate because the nebulizer recognizes the identifier associated with the vial assembly (a used vial assembly). A vial identifier has a unique serial number programmed therein at the chip manufacturer, and the active mesh nebulizer tracks vial usage using the unique serial number in the identifier 113 to prevent vial re-use.

FIG. 11 is a flow diagram of a method 1100 of operating an active mesh nebulizer, in accordance with some embodiments. The method 1100 begins with step 1102 when a user inserts a vial assembly cartridge into the nebulizer. In step 1104, the nebulizer reads medication information from the vial assembly using a bar code reader, RFID, wired pin connector, or any other suitable data communication method. In step 1106, using the medication information, the nebulizer verifies that the medication is authorized. In step 1108, if the medication is authorized, the nebulizer dispenses an appropriate dose of medicine. In accordance with some embodiments, the nebulizer includes a conductivity sensor and/or pH sensor where the sensor extends into the vial volume on the liquid-side of the nebulizer mesh/grid. By measuring the conductivity and/or pH of a fluid, the measured value is compared to a "calibrated" value of the fluid as prepared at the packaging plant. When there is a match, the nebulizer operates. When there is a mismatch, the nebulizer does not operate. This prevents the nebulizer from dispensing medicine when the original fluid has been replaced. In some embodiments, the match is determined before the vial identifier has been read. In some embodiments, the match is determined before the vial identifier has been read. The user inhales the medication in step 1110.

For a single fluid having a given viscosity, by increasing the voltage applied to the nebulizer grid, the rate at which the liquid is converted into droplets increases. Liquids with different viscosities require different grid vibrational frequencies and/or supply voltages from the power supply (see power supply 128) in order to become plume particles. In some embodiments, a liquid with a lower viscosity is converted to a plume of particles with a lower vibrational frequency. In some embodiments, a liquid with a higher viscosity is converted to a plume of particles with a higher vibrational frequency than a liquid with lower viscosity, and, therefore, needs a higher grid voltage to make the particle plume. The voltage applied to the grid is regulated by a voltage regulating circuit in the nebulizer.

What is claimed is:

1. A method of treating a patient's respiratory system tissue, comprising:
   generating a plume of particles of a treating solution from a nebulizer, wherein
      the nebulizer generates the plume of particles for a vibrational time period,
      the treating solution is a solution of at least 40% ethyl alcohol, by volume, and
      the particles comprising the plume of particles have a diameter greater than 10 micrometers (μm)
   applying the plume of particles to the patient's respiratory system solely through the patient's nose during an intermediate portion of the patient's inhalation;
   pausing the patient's respiration for 3-10 seconds to allow a first volume of the particles to deposit on the patient's respiratory system tissue;
   removing an undeposited portion of the particles from the patient's respiratory system by exhalation;
   determining whether the first volume of deposited particles comprises a treatment volume sufficient to induce germicidal action on the patient's respiration system tissue; and
   if the treatment volume has not been reached, repeating the operations of applying the plume of particles to the patient's respiratory system, pausing the patient's respiration, and removing the undeposited portion of the particles from the patient's respiratory system until the treatment volume has been reached.

2. The method of claim 1, further comprising
   determining whether the treatment volume of the treating solution has been delivered to the patient's respiratory system based on a total of the vibrational time periods used to generate the plume of particles of the treatment solution during the operation of applying the plume of particles to the patient's respiratory system.

3. The method of claim 1, wherein generating a plume of particles of a treating solution from a nebulizer further comprises generating a plume of particles of a treating solution from a pot-type nebulizer.

4. The method of claim 1, wherein generating a plume of particles of a treating solution from a nebulizer further comprises generating a plume of particles of a treating solution from an active mesh nebulizer having a vibratable piezoelectric plate therein.

5. The method of claim 1,
   wherein determining whether the treatment volume of the treating solution has been delivered further comprises monitoring a solution level in a reservoir of a nebulizer, and further comprising halting treatment when the treatment volume of the treating solution has been delivered.

6. The method of claim 5, wherein determining whether the treatment volume of the treating solution has been delivered further comprises determining that a patient has inhaled at least 1 milliliter (ml) of the treating solution from the nebulizer.

7. The method of claim 1, wherein determining whether the treatment volume of the treating solution has been delivered further comprises deactivating the nebulizer after not more than five activations of a vibratable piezoelectric plate in the nebulizer.

8. The method of claim 7, wherein determining whether the treatment volume of the treating solution has been delivered further comprises determining that the not more than five activations of the vibratable piezoelectric plate in the nebulizer have nebulized at least 0.2 milliliter (ml) of the treating solution, and determining that the particles from the not more than five activations have been inhaled by a patient.

9. The method of claim 1, wherein generating a plume of particles of a treating solution from a nebulizer further comprises generating a plume of particles of a treating solution comprising at least 60% ethyl alcohol, by volume.

10. The method of claim 1, wherein generating a plume of particles of a treating solution from a nebulizer further comprises generating a plume of particles of a treating solution comprising at least 70% ethyl alcohol, by volume.

11. The method of claim 1, wherein generating a plume of particles of a treating solution from a nebulizer further comprises generating a plume of particles of a treating solution comprising at least 80% ethyl alcohol, by volume.

12. The method of claim 1, further comprising:
selecting a portion of the patient's respiratory system for treatment; and
selecting, based on the selected portion of the respiratory system, a nebulizer configured to produce the plume of particles targeting the selected portion of the respiratory system.

13. The method of claim 1, further comprising
detecting particles on respiratory system tissues; and
regulating inhaling particles of the treating solution by changing inhalation speed.

14. The method of claim 1, further comprising
detecting irritation in the nasal passages during inhaling the particles; and
regulating inhaling particles of the treating solution by decreasing inhalation speed.

15. The method of claim 1, further comprising
detecting irritation in the nasal passages during inhaling the particles; and
regulating inhaling particles of the treating solution by increasing inhalation speed.

16. The method of claim 1, further comprising
detecting irritation in the nasal passages during inhaling the particles; and
regulating particle distribution by changing a duration of inhaling particles of the treating solution.

17. The method of claim 16, further comprising wherein changing the duration of inhaling the particles further comprises increasing the duration of inhaling the particles.

18. The method of claim 16, further comprising decreasing the duration of inhaling the particles.

* * * * *